United States Patent
Lin et al.

(10) Patent No.: US 9,029,332 B2
(45) Date of Patent: May 12, 2015

(54) CROSS-LINKED PEPTIDES AND PROTEINS, METHODS OF MAKING SAME, AND USES THEREOF

(75) Inventors: Qing Lin, Getzville, NY (US); Avinash Muppidi, Buffalo, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 99 days.

(21) Appl. No.: 13/994,296

(22) PCT Filed: Dec. 15, 2011

(86) PCT No.: PCT/US2011/065282
§ 371 (c)(1),
(2), (4) Date: Nov. 11, 2013

(87) PCT Pub. No.: WO2012/083078
PCT Pub. Date: Jun. 21, 2012

(65) Prior Publication Data
US 2014/0057857 A1    Feb. 27, 2014

Related U.S. Application Data

(60) Provisional application No. 61/459,569, filed on Dec. 15, 2010.

(51) Int. Cl.
| | | |
|---|---|---|
| *A61K 38/12* | (2006.01) | |
| *C07K 7/56* | (2006.01) | |
| *C07K 1/107* | (2006.01) | |
| *C07K 7/08* | (2006.01) | |
| *C07K 14/47* | (2006.01) | |

(52) U.S. Cl.
CPC ............... *C07K 7/56* (2013.01); *C07K 1/1077* (2013.01); *C07K 7/08* (2013.01); *C07K 14/4747* (2013.01); *C07K 2319/95* (2013.01); *C07K 2319/00* (2013.01)

(58) Field of Classification Search
CPC ..................................................... A61K 38/00
See application file for complete search history.

(56) References Cited

U.S. PATENT DOCUMENTS

| | | | |
|---|---|---|---|
| 5,446,128 | A | 8/1995 | Kahn |
| 5,710,245 | A | 1/1998 | Kahn |
| 5,859,184 | A | 1/1999 | Kahn et al. |
| 7,183,059 | B2 | 2/2007 | Verdine et al. |
| 7,192,713 | B1 | 3/2007 | Verdine et al. |
| 7,202,332 | B2 | 4/2007 | Arora et al. |
| 7,723,469 | B2 | 5/2010 | Walensky et al. |
| 7,863,239 | B2 | 1/2011 | Timmerman et al. |
| 7,960,506 | B2 | 6/2011 | Nash |
| 7,981,998 | B2 | 7/2011 | Nash |
| 7,981,999 | B2 | 7/2011 | Nash |
| 2003/0125262 | A1 | 7/2003 | Kiessling et al. |
| 2005/0250680 | A1 | 11/2005 | Walensky et al. |
| 2006/0008848 | A1 | 1/2006 | Verdine et al. |
| 2006/0073518 | A1 | 4/2006 | Timmerman et al. |
| 2007/0207947 | A1 | 9/2007 | Frank et al. |
| 2008/0262200 | A1 | 10/2008 | Nash |
| 2008/0313749 | A1 | 12/2008 | Timmerman et al. |
| 2009/0047711 | A1 | 2/2009 | Nash |
| 2009/0088553 | A1 | 4/2009 | Nash |
| 2009/0149630 | A1 | 6/2009 | Walensky et al. |
| 2009/0275519 | A1 | 11/2009 | Nash et al. |
| 2009/0326192 | A1 | 12/2009 | Nash et al. |
| 2010/0093086 | A1 | 4/2010 | Lin et al. |
| 2010/0184628 | A1 | 7/2010 | Nash |
| 2010/0210515 | A1 | 8/2010 | Nash et al. |
| 2010/0216688 | A1 | 8/2010 | Nash et al. |
| 2010/0298201 | A1 | 11/2010 | Nash et al. |
| 2011/0144303 | A1 | 6/2011 | Nash et al. |
| 2011/0223149 | A1 | 9/2011 | Nash et al. |
| 2011/0263815 | A1 | 10/2011 | Nash |

FOREIGN PATENT DOCUMENTS

| | | |
|---|---|---|
| WO | 9700267 A1 | 1/1997 |
| WO | 2008095063 A1 | 8/2008 |
| WO | 2009108261 A2 | 9/2009 |
| WO | 2010011313 A2 | 1/2010 |

OTHER PUBLICATIONS

Blackwell et al., Highly Efficient Synthesis of Covalently Cross-Linked Peptide Helices by Ring-Closing Metathesis, Angew. Chem. Int. Ed. 1998, 37, 3281-3284.
Schafmeister et al., An All-Hydrocarbon Cross-Linking System for Enhancing the Helicity and Metabolic Stability of Peptides, J. Am. Chem. Soc. 2000, 122, 5891-5892.
Walensky et al., Activation of Apoptosis in Vivo by a Hydrocarbon-Stapled BH3 Helix, Science 2004, 305, 1466-1470.
Bautista et al., Bridged (beta)3-Peptide Inhibitors of p53-hDM2 Complexation: Correlation between Affinity and Cell Permeability, J. Am. Chem. Soc. 2010, 132, 2904-2906.
Kumita et al., Photo-control of helix content in a short peptide, Proceedings of the National Academy of Sciences, vol. 97, No. 8, pp. 3803-3808. Apr. 11, 2000.
Muppidi et al., Conjugation of spermine enhances cellular uptake of the stapled peptide-based inhibitors of p53-Mdm2 interaction, Bioorganic & Medicinal Chemistry Letters, vol. 21, No. 24, pp. 7412-7415. Oct. 4, 2011.

(Continued)

*Primary Examiner* — Marcela M Cordero Garcia
*Assistant Examiner* — Kaipeen Yang
(74) *Attorney, Agent, or Firm* — Hodgson Russ LLP

(57) ABSTRACT

Cross-linked proteins and peptides, and methods of making and uses of such cross-linked proteins and peptides. The cross-linked proteins and peptides have rigid, distance-matching bismethylene aryl cross-linking moieties. Compositions comprising the cross-linked proteins and peptides can be used as pharmaceutical delivery formulations. The cross-linked proteins and peptides can have improved properties, such as cell permeability, as compared to the parent protein or peptide.

12 Claims, 14 Drawing Sheets

(56) References Cited

OTHER PUBLICATIONS

Muppidi et al., Achieving cell penetration with distance-matching cysteine cross-linkers: a facile route to cell-permeable peptide dual inhibitors of Mdm2/Mdmx, Chemical Communications, vol. 47, No. 33, p. 9396. Jan. 1, 2011.

Teeling et al., The Biological Activity of Human CD20 Monoclonal Antibodies Is Linked to Unique Epitopes on CD20, The Journal of Immunology, 2006, vol. 177, pp. 362-371.

Timmerman et al., Binding of CDR-derived peptides is mechanistically different from that of high-affinity parental antibodies, Journal of Molecular Recognition, 2010, vol. 23, pp. 559-568.

Timmerman et al., A Combinatorial Approach for the Design of Complementarity-determining Region-derived Peptodimimetics with in Vitro Anti-tumoral Activity, The Journal of Biological Chemistry, Dec. 4, 2009, vol. 284, No. 49, pp. 34126-34134.

Timmerman et al., Rapid and Quantitative Cyclization of Multiple Peptide Loops onto Synthetic Scaffolds for Structural Mimicry of Protein Surfaces, ChemBioChem, 2005, vol. 6, pp. 821-824.

Timmerman et al., Functional reconstruction and synthetic mimicry of a conformational epitope using CLIPS(TM) technology, Journal of Molecular Recognition, 2007, vol. 20, pp. 283-299.

Timmerman et al., Functional Reconstruction of Structurally Complex Epitopes using CLIPS(TM) Technology, Vaccine Development Conference held at the University of Pittsburgh on Sep. 28-30, 2008, 14 pages, (http://www.biacore.com/lifesciences/events/vaccine2008/home/index.html).

Sun et al., The Cystine-Knot Growth-Factor Superfamily, Annu. Rev. Biophys. Biomol. Struct., 1995, vol. 24, pp. 269-291.

Zhang et al., Stabilization of Folded Peptide and Protein Structures via Distance Matching with a Long, Rigid Cross-Linker, J. Am. Chem. Soc., 2007, vol. 129, pp. 14154-14155.

CROSS-LINKED PEPTIDES AND PROTEINS, METHODS OF MAKING SAME, AND USES THEREOF

CROSS-REFERENCE TO RELATED APPLICATIONS

This application claims priority to U.S. provisional patent application No. 61/459,569, filed Dec. 15, 2010, the disclosure of which is incorporated herein by reference.

FIELD OF THE INVENTION

The present invention is related to cross-linked peptides and proteins, method of making such peptides and proteins, and uses of same. More particularly, the invention relates to peptides and proteins cross linked through cysteine and methylcysteine residues.

BACKGROUND OF THE INVENTION

Despite their excellent bioactivity, peptides are rarely good drug candidates because they cannot penetrate cell membrane to reach their intracellular target. A growing number of chemical strategies have been developed recently to convert peptides into cell-permeable bioactive ligands targeting the intracellular protein-protein interactions. These include the use of alternative backbones such as β-peptides, the incorporation of α,α-dialkylamino acids such as Aib, the side chain-to-side chain cross linking via the lactam, hydrocarbon, or heterocyclic bridges, the backbone-to-side chain cross linking; and the use of low molecular weight peptidomimetics such as terphenyl-based helix mimics. Another strategy to impart peptides with improved cell permeability is to fuse peptides with the cell penetrating peptide (CPP) sequences. A drawback to the CPP-fusion approach is that significant mass needs to be added to the peptide.

Though these strategies have generated peptide analogs with the improved cell permeability, extensive chemical modifications were typically required. For example, hydrocarbon cross linking involves the introduction of two chiral α,α-dialkylamino acids carrying the olefin side chains and the subsequent ruthenium-catalyzed ring closing metathesis, which often produces a mixture of Z- and E-olefin linkages.

BRIEF SUMMARY OF THE INVENTION

The present invention provides cross-linked proteins and peptides, where the cross link is formed between two cysteines or α-methylcysteines at the i and i+7 positions of the protein or peptide. The cross link is formed through a cysteine-alkylation reaction with a rigid, distance-matching cross linker. The cross-linked proteins and peptides have at least one cross link formed by a rigid, distance matching cross-linking bismethylene aryl moiety. The cross-linked peptides or proteins can have at least a partial helical structure. The cross-linked protein or peptides can have improved properties as compared to the parent (or the analogous non-cross-linked protein or peptide). For example, the cross-linked peptides can have improved penetration into cells with low cytotoxicity, the cross-linked peptides show increased enzymatic stability, and the cross-linked peptides or peptides exhibit improved biological activity.

In an embodiment, the protein or peptides have the following structure:

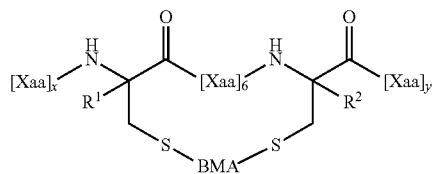

where [$X_{aa}$] is any amino acid. In the case of peptides, x is an integer from 0 to 42, including all integer values and ranges therebetween, y is an integer from 0 to 42, including all integer values and ranges therebetween, and x+y is less than or equal to 42, including all integer values and ranges therebetween. In the case of proteins, x+y is greater than or equal to 43. BMA is a bismethylene aryl moiety and is connected to the protein or peptide through two thioether bonds. $R^1$ and $R^2$ are each independently hydrogen or an alkyl group having from 1 to 15 carbons.

The present invention also provides methods for making cross-linked peptides or proteins. In an embodiment, the method for preparation of cross-linked peptides or proteins comprises the steps of (a) providing a peptide or protein having the following structure:

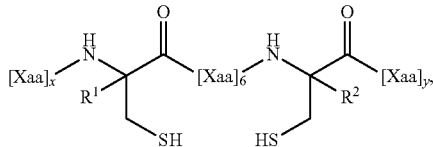

where [$X_{aa}$] is any amino acid In the case of peptides, x is an integer from 0 to 42, y is an integer from 0 to 42, and x+y is less than or equal to 42. In the case of proteins, x+y is greater than or equal to 43. $R^1$ and $R^2$ are each independently hydrogen or an alkyl group, (b) contacting said peptide to a bismethylene aryl linker, such that a cross-linked peptide or protein having the following structure:

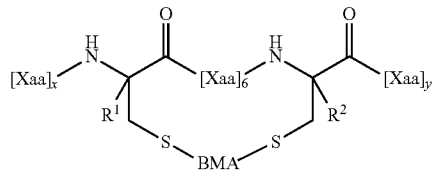

is formed.

The present invention also provides compositions comprising the cross-linked peptides or proteins of the present invention. In an embodiment, the composition comprises one or more cross-linked peptides or proteins of the present invention and one or more excipients.

DETAILED DESCRIPTION OF THE INVENTION

The present invention provides cross-linked peptides and proteins, methods of making such peptides and proteins, and uses thereof. For example, the peptides can be used in pharmaceutical formulations, which can be used to administer the peptides. This disclosure describes a new cross-linking chemistry that, for example, improves cell permeability of the cross-linked peptides and proteins.

The present invention provides cross-linked proteins and peptides, where the cross link is formed between two cysteines or α-methylcysteines at the i and i+7 positions of the protein or peptide. The cross link is formed through a cysteine-alkylation reaction with a rigid, distance-matching cross linker.

Figure 1:
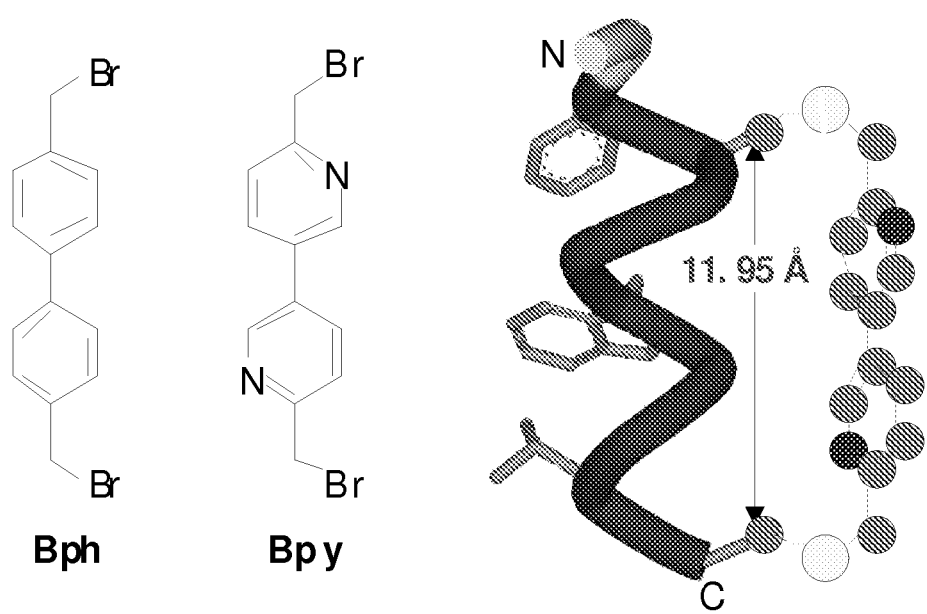
FIG. 1. Structures of the rigid cysteine cross linkers Bph and Bpy (left), and a model of Bpy cross-linked peptide dual inhibitor (right) with two cysteines separated by a distance of 11.95 Å.

For example, the use of bisarylmethylene bromides as rigid, distance-matching cysteine cross linkers (FIG. 1) is disclosed herein. By cross linking a peptide dual inhibitor (PDI) of p53-MDM2/MDMX interactions with two cysteines located at i, and i+7 positions, enhancement in cell penetration without apparent cytotoxicity was observed. Additionally, increases in peptide helicity and bioactivity were observed. Because cysteines can be readily introduced into proteins and peptides, this cysteine cross-linking chemistry also provides a facile route to deliver bioactive peptides and proteins into cells without significant addition of mass.

The term "alpha(α)-amino acid" or simply "amino acid" refers to a molecule containing both an amino group and a carboxyl group bound to a carbon which is designated as the α-carbon. Suitable amino acids include, but are not limited to, both the D- and L-isomers of the amino acids and amino acids prepared by organic synthesis or other metabolic routes. Unless the context specifically indicates otherwise, the term amino acid, as used herein, is intended to include amino acid analogs. Examples of suitable amino acids also include, "naturally occurring amino acids", which refers to any one of the twenty amino acids commonly found in peptides synthesized in nature, and known by the one letter abbreviations A, R, N, C, D, Q, E, G, H, I, L, K, M, F, P, S, T, W, Y, and V.

The term "amino acid analog" refers to a molecule which is structurally similar to an amino acid and which can be substituted for an amino acid in the formation of a cross-linked peptide. Amino acid analogs include, without limitation, compounds which are structurally identical to an amino acid, as defined herein, except for the inclusion of one or more additional methylene groups between the amino and carboxyl group (e.g., β-amino acids), or for the substitution of the amino or carboxy group by a similarly reactive group (e.g., substitution of the primary amine with a secondary or tertiary amine, or substitution the carboxy group with an ester), or α,α-disubstituted amino acids (e.g., α-alkyl substituted amino acids, such as α-methylcysteine). Unless the context specifically indicates otherwise, the term amino acid, is intended to include amino acid analogs.

The term "amino acid residue" refers to an amino acid that is part of a protein or peptide. The residues are amino acids connected to other amino acid resides through a peptidic bond or bonds to form proteins or peptides. Unless the context specifically indicates otherwise, the term amino acid, is intended to include amino acid resides.

The term "cross linked" as used herein refers to the intramolecular connection of two cysteine or α-alkylcysteine (e.g., α-methylcysteine residues), where the residues are at the i and i+7 positions of a protein or peptide. i denotes a cysteine residue in the protein or peptide sequence and i+7 denotes a cysteine residue 7 amino acid residues away from the cysteine at the i position. There are six (6) amino acids between the two cysteine residues.

The term "aryl" includes both aryl ring systems and heteroaryl ring systems and is a 10 to 14 carbon multicyclic (e.g., bicyclic, or tricyclic) aromatic ring system. The ring system can unsubstituted or substituted. For example, depending on the structure of the ring system, 2, 3, 4, 5, or 6 atoms of each individual ring can be substituted by a substituent. For example, a bicyclic or tricyclic ring system can also be substituted with 0-2 heteroatoms, the heteroatom being a nitrogen. The rings of the ring system can be fused (e.g., phenanthrene, 9,10-dihydrophenanthrene, benzoisoquinoline) or separated by a single bond (e.g., biphenyl, bipyridine, phenylpyridine).

The term "protein" as used herein refers to an amino acid chain, where the chain has greater than 50 amino acid residues, which can be obtained, for example, from either chemical synthesis or DNA-based recombinant methods.

The term "peptide" as used herein refers to an amino acid chain, where the chain has from 8 to 50 amino acid residues.

The term "structural stabilization" as used herein refers to the maintenance of a defined secondary structure of peptides or proteins in solution by chemical cross linking as described herein, which can be measured by circular dichroism (CD), NMR or another biophysical measure, or resistance to proteolytic degradation in vitro or in vivo. As used herein, the term "helical stability" refers to the maintenance of a helical structure by a cross-linked helical peptide of the invention. For example, the helical stability can be measured by circular dichroism.

The term "enzymatic stability" as used herein refers to the ability of the peptides or proteins to stay intact in the presence of an enzyme having proteolytic activity such as trypsin and chymotrypsin in biological buffers or in human serum. For example, the proteolytic stability of the peptides can be measured by high-performance liquid chromatography (HPLC) and mass spectrometry.

In an aspect, the present invention provides cross-linked peptides and proteins. In an embodiment, the protein or peptides have the following structure:

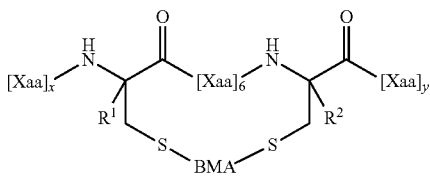

where $[X_{aa}]$ is any amino acid. In the case of peptides, x is an integer from 0 to 42, including all integer values and ranges therebetween, y is an integer from 0 to 42, including all integer values and ranges therebetween, and x+y is from 0 to 42, including all integer values and ranges therebetween. In the case of proteins, x+y is greater than or equal to 43. BMA is a bismethylene aryl moiety. $R^1$ and $R^2$ are each independently hydrogen or an alkyl group having from 1 to 15 carbons, including all integer numbers of carbons and ranges therebetween. Examples of a suitable alkyl group include, but are not limited to, methyl, ethyl, propyl, isopropyl, and butyl groups. In another embodiment, the cross-linked structure represented in this structure is a structural subpart (i.e., structural motif) of a protein.

One having skill in the art would understand that the terminal amino acids of the protein or peptide has an amino group or carboxylic acid (or a salt thereof). For example, in the structures herein when x is 0 that terminus of the protein or peptide is an amino group, and when y is 0 that terminus of the protein or peptide is a carboxylic acid.

The cross-linked peptides can have from 8 to 50 amino acid residues, including all integer values and ranges therebetween. The cross-linked proteins have lengths greater than 50 amino acid residues. It is desirable that the cross-linked protein be soluble in aqueous solvents at physiological pH values (e.g., biological buffers, blood or serum) and be less than 100 kDa. The cross-linked protein or peptide has at least two cysteine residues, where these cysteine residues are at the i and i+7 positions of the protein or peptide (i.e., there are six amino acid residues between these two cysteine residues). In an embodiment, the cross-linked peptide or protein has only two cysteine residues.

It is considered that any protein or peptide, with appropriately placed cysteines (naturally occurring or introduced) can be cross-linked. It is desirable that the proteins and peptides exhibit biological activity. Examples of suitable proteins include, but are not limited to, growth factors and chemokines. In an embodiment, the cross-linked peptide is a cross-linked PDI peptide. In another embodiment, the cross-linked peptide is a cross-linked Noxa peptide, a segment of the pro-apoptotic BH3-only protein Noxa.

In an embodiment, the amino acids and amino acid analogs are of the D-configuration. In another embodiment, amino acids and amino acid analogs are of the L-configuration. In yet another embodiment, some of the amino acids and amino acid analogs contained in the protein or peptide are of the D-configuration while some of the amino acids and amino acid analogs are of the L-configuration.

The proteins or peptides of the present invention can have, for example, one or more asymmetric centers, and thus, occur as racemates and racemic mixtures, single enantiomers, individual diastereomers or diastereomeric mixtures. All such isomeric forms of these proteins or peptides are included in the present invention unless expressly provided otherwise. The proteins or peptides can also represented in multiple tautomeric forms, in such instances, the invention includes all tautomeric forms of the compounds described herein. All such isomeric forms of such compounds are included in the present invention unless expressly provided otherwise. All crystal forms of the compounds described herein are included in the present invention unless expressly provided otherwise.

In an embodiment, the protein or peptide is conjugated to a fluorophore. For example, a protein or peptide can be conjugated to a fluorescein or fluorescein isothiocyanate (FITC) molecule. The fluorophore can be conjugated to the protein or peptide through a linker such as, for example, aminohexanoic acid (Ahx).

In an embodiment, the two cysteine residues in the cross-link of the peptide or protein are both of the R- or S-configuration (i.e., which can also be described by the appropriate L or D notation) or one stereocenter is R and the other is S.

In an embodiment, the cysteine residues used to form the cross link have α-alkyl groups having from 1 to 15 carbons, including all integer numbers of carbons and ranges therebetween, at the α-carbon of the cysteine residues. Examples of a suitable alkyl group include, but are not limited to, methyl, ethyl, propyl, isopropyl, or butyl groups.

The cross-linked proteins and peptides have at least one cross link formed by a rigid, distance matching cross-linking bismethylene aryl moiety. The cross link forms a macrocyclic ring, which is not part of the core (i.e., it is exogeneous) or inherent structure of the protein or peptide. The macrocyclic ring is comprised of a bismethylene aryl moiety and includes 8 amino acids of the protein or peptide, two of which are cysteine residues connected to the bismethylene aryl moiety through thioether bonds. For example, a protein can have from 1, 2 or 3 cross links. As another example, a protein can have one or more domains (e.g., domains of 10 to 50 amino acids), and each domain can have 1, 2, or 3 cross links.

It is considered that the bismethylene aryl moieties are of a size and/or rigidity that provide desirable stabilization of a helical motif of a peptide or a helical segment of a protein. Without intending to be bound by any particular theory, it is considered the distance matching and/or rigidity of the bismethylene aryl moiety is such that the cross-linked protein or peptide has increased helicity and increased cell permeability relative to proteins and peptides that are not cross linked according to the present invention.

The bismethylene aryl (BMA) moiety has an aryl moiety and is connected to the protein or peptide through two thioether bonds. In an embodiment, the cross-linking moiety comprises a bismethylene aryl moiety having two phenyl rings connected by a single bond. For example, the bismethylene aryl moiety can be represented by the following:

where Z can be nitrogen or carbon. The aryl rings of the bismethylene aryl moiety can be substituted or unsubstituted. When the aryl rings are unsubstituted, the aryl rings do not have any R substituents. When the aryl rings are substituted, depending on the aryl moiety, the bismethylene aryl moiety can have one or more R substituents. For example, in the bismethylene aryl ring structure shown above, the each aryl ring of the structure can have 1, 2, 3 or 4 (where Z is a carbon) R substituents. The R substituents are halogens (F, Cl, Br, or I), alkyl groups (having from 1 to 15 carbons, including all integer values of carbons and ranges therebetween), alkoxy groups (wherein the alkyl moiety of the alkoxy group has from 1 to 15 carbons, including all integer values of carbons and ranges therebetween), nitro groups, amino groups, alkylamino groups (wherein the alkyl moiety or moieties of the alkylamino group, independently, has from 1 to 15 carbons, including all integer values of carbons and ranges therebetween), trifluoromethyl groups, or combinations thereof.

In an embodiment, two R groups (one from each aryl ring) are joined to form a fused ring structure. The ring formed by the joining of two R groups can have 5, 6, or 7 carbons. Examples of such structures are represented in the following:

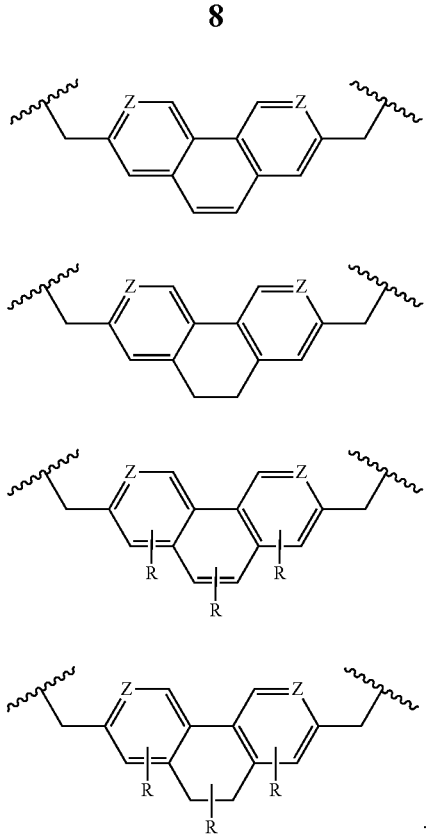

The aryl rings of these structures can be substituted or unsubstituted as described herein.

It is desirable that the aryl structure is symmetrical so that only one isomer (e.g., diastereomer) of the cross-linked peptide is formed due to symmetry-related degeneration. For example, in the structures where Z is nitrogen, it is desirable the aryl portion of the moiety be symmetrical (e.g., biphenyl, bipyridine, and phenanthroline, etc.) and not unsymmetrical (e.g., benzoisoquinoline) as to not form isomers.

In various embodiments, the protein or peptide has one of the following structure:

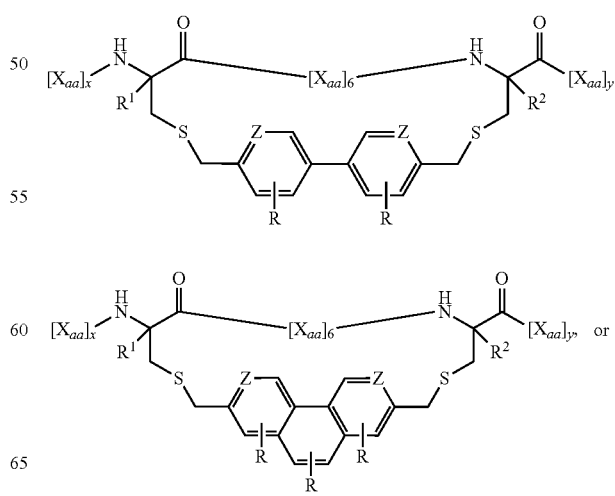

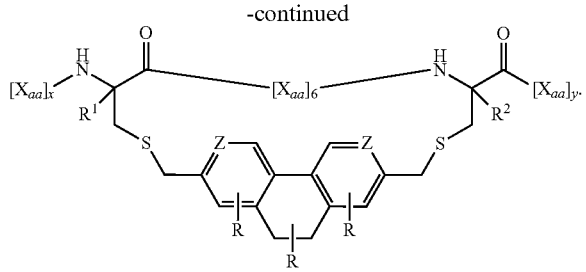

When the aryl rings are unsubstituted, the aryl rings do not have any R substituents. R, $R^1$, and $R^2$ are as described herein.

In various embodiments, the protein or peptide has the following structure:

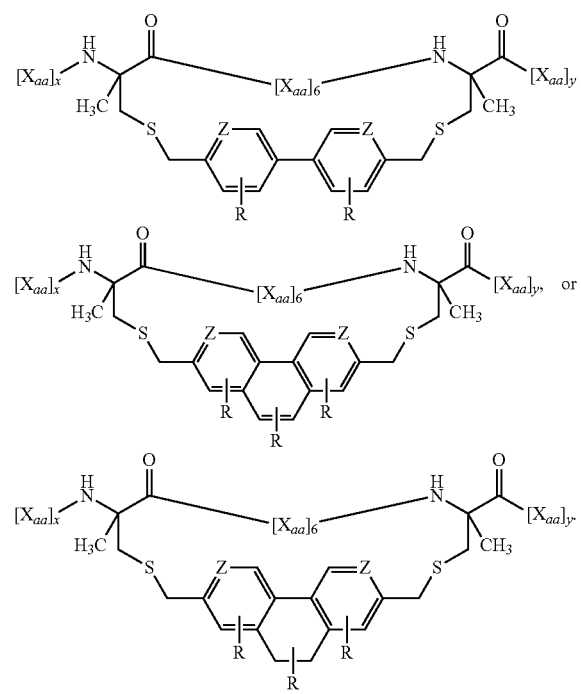

When the aryl rings are unsubstituted, the aryl rings do not have any R substituents. R, $R^1$, and $R^2$ are as described herein.

In various embodiments, the cross-linked peptides are:
LTFCHYWAQLCS (SEQ ID NO:2),
LTFCRYWARLCS (SEQ ID NO:3),
LTFcHYWAQLCS (SEQ ID NO:4),
LTFcRYWARLCS (SEQ ID NO:5),
AACLRRIGDCVNLRQKLLN (SEQ ID NO:6),
AAcLRRIGDCVNLRQKLLN (SEQ ID NO:7),
AAQLRCIGDKVNCRQKLLN (SEQ ID NO:8),
AACLRRIGDCVNLRQKLLNSQPKKKRKV (SEQ ID NO:9),
$AAC_m$LRRIGD$C_m$VNLRQKLLN (SEQ ID NO:10),
AAcLRRIGDCVNLRQKLLNSQPKKKRKV (SEQ ID NO:11),
AACLRAIGDCVNLAQALLN (SEQ ID NO:12), or
AAcLRAIGDCVNLAQALLN (SEQ ID NO:13),
and the BMA is Bph and is connected to the c, C, or $C_m$ residues,
LTFCHYWAQLCS (SEQ ID NO:2),
LTFCRYWARLCS (SEQ ID NO:3),
LTFcHYWAQLCS (SEQ ID NO:4),
LTFcRYWARLCS (SEQ ID NO:5),
AACLRRIGDCVNLRQKLLN (SEQ ID NO:6), or
AAcLRRIGDCVNLRQKLLN (SEQ ID NO:7),
and the BMA is Bpy and is connected to the c or C residues,
AACLRRIGDCVNLRQKLLN (SEQ ID NO:6),
and the BMA is Bdp and is connected to the C residues,
AACLRRIGDCVNLRQKLLN (SEQ ID NO:6),
and the BMA is Bdb and is connected to the C residues,
AACLRRIGDCVNLRQKLLN (SEQ ID NO:6),
and the BMA is Bphe and is connected to the C residues, and
where, c is D-cysteine, C is L-cysteine, and $C_m$ is α-methyl-cysteine.

In various embodiments, the cross-linked peptides are:
FITC-Ahx-AACLRRIGDCVNLRQKLLN (SEQ ID NO:6)
FITC-Ahx-AAcLRRIGDCVNLRQKLLN (SEQ ID NO:7)
FITC-Ahx-AAQLRCIGDKVNCRQKLLN (SEQ ID NO:8)
FITC-Ahx-AA$C_m$LRRIGD$C_m$VNLRQKLLN (SEQ ID NO:10)
and the BMA is Bph and is connected to the c, C, or $C_m$ residues,
Fluorescein-Ahx-LTFCHYWAQLCS (SEQ ID NO:2)
Fluorescein-Ahx-LTFCRYWARLCS (SEQ ID NO:3)
Fluorescein-Ahx-LTFcHYWARLCS (SEQ ID NO:5)
Fluorescein-Ahx-LTFcRYWARLCS (SEQ ID NO:5)
FITC-Ahx-AAcLRRIGDCVNLRQKLLN (SEQ ID NO:7)
and the BMA is Bpy and is connected to the c, C, or $C_m$ residues,
where c is D-cysteine, C is L-cysteine, $C_m$ is α-methyl cysteine, and Ahx is aminohexanoic acid.

In an embodiment, the cross-linked protein is:

(SEQ ID NO: 14)
GSSHHHHHHSSGLVPRGSHMPADLKDEAA<u>C"</u>LRRIGD<u>C"</u>VNLRQKLLNGG

GGSGGGGSGGGGSMQIFVKTLTGKTITLEVEPSDTIENVKAKIQDKEGIP

PDQQRLIFAGKQLEDGRTLSDYNIQKESTLHLVLRLRGG, where the BMA moiety is connected to the <u>C"</u> residues.

The cross-linked peptides or proteins can have at least a partial helical structure. For example, a cross-linked peptide can have a helical structure (or multiple helical structures), and each helical structure is stabilized by a single cross link or multiple (e.g., two or three) cross links. As another example, a protein can have a helical motif (or multiple helical motifs), and each motif is stabilized by a single cross link or multiple (e.g., two or three) cross links. When the protein has a helical segment or the peptide is a helical peptide, the bismethylene aryl moiety is part of the exogenous macrocyclic ring that connects two cysteines of the helical protein or peptide. The amino acids i to i+7 are included in the macrocyclic ring.

The cross-linked peptides can have greater percent helicity as compared to the linear parent peptide (non-cross-linked peptide). For example, the cross-linked peptides exhibit 14-34% percent helicity with 19 residues compared to only 9% percent helicity for the parent linear peptide. In another embodiment, the cross-linked peptides exhibit 14-20% percent helicity with 12 amino acid residues compared to only 11-13% percent helicity for the parent linear peptides. In various embodiments, the cross-linked peptides exhibit at least a 1.25, 1.5, 1.75 or 2-fold increase in α-helicity as determined by circular dichroism compared to a corresponding non-cross-linked peptide.

The cross-linked protein can have one or more helical motifs. For example, a helical motif of a protein can have from 10 to 50 amino acids, including all integer values and ranges therebetween. For example, a cross-linked protein can have a single helical motif or multiple helical motifs and each helical motif can have one or multiple cross links.

The cross-linked protein or peptides can have improved properties as compared to the parent (or the analogous non-cross-linked protein or peptide). For example, the cross-linked peptides can have improved penetration into cells with low cytotoxicity. Additionally, the cross-linked peptides show increased enzymatic stability (e.g., proteolytic stability against proteases such as trypsin and chymotrypsin). Further, the cross-linked peptides or peptides exhibit improved biological activity (such inhibitory activities against protein-protein interactions, or agonist activities toward cell surface receptors).

In another aspect, the present invention provides methods for making cross-linked peptides or proteins. Cross-linked peptides or proteins of the present invention can be made using the methods. In an embodiment, the method for preparation of cross-linked peptides or proteins comprises the steps of (a) providing a peptide or protein having the following structure:

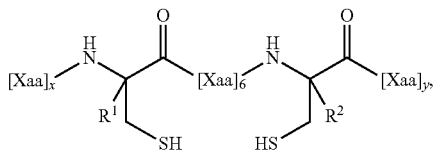

where $[X_{aa}]$ is any amino acid. In the case of peptides, x is an integer from 0 to 42, including all integer values and ranges therebetween, y is an integer from 0 to 42, including all integer values and ranges therebetween, and x+y is 0 to 42, including all integer values and ranges therebetween. In the case of proteins, x+y is greater than or equal to 43. $R^1$ and $R^2$ are each independently hydrogen or an alkyl group having from 1 to 15 carbons, including all integer numbers of carbons and ranges therebetween, such as, for example, methyl, ethyl, propyl, isopropyl, and butyl groups. In another embodiment, the cross-linked structure represented in this structure is a structural subpart (i.e., structural motif) of a protein, (b) contacting said peptide to a bismethylene aryl linker, such that a cross-linked peptide or protein having the following structure:

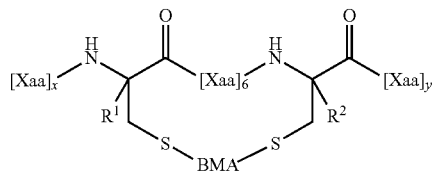

is formed.

In an embodiment, the present invention provides cross-linked peptides or proteins of the present invention made using the methods disclosed herein.

It is considered that any protein or peptide, with appropriately placed cysteines (naturally occurring or introduced) can be cross-linked. It is desirable that the proteins and peptides exhibit biological activity. Suitable proteins or peptides can be made by methods known in the art. Examples of suitable proteins include, but are not limited to, growth factors and chemokines. In an embodiment, the cross-linked peptide is a cross-linked PDI peptide. In another embodiment, the cross-linked peptide is a cross-linked Noxa peptide, a segment of the pro-apoptotic BH3-only protein Noxa.

The peptides can have from 8 to 50 amino acid residues, including all integer values and ranges therebetween. The proteins have lengths greater than 50 amino acid residues. The protein or peptide has at least two cysteine residues, where these cysteine residues are at the i and i+7 positions of the protein or peptide (i.e., there are six amino acid residues between these two cysteine residues). In an embodiment, the peptide or protein has only two cysteine residues.

The bismethylene aryl linker has an aryl moiety and two suitable leaving groups. In an embodiment, the bismethylene aryl linker has the following structure:

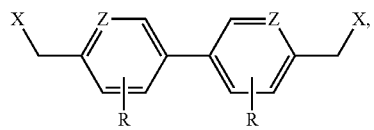

where X is a suitable leaving group (LG) substituent and Z can be nitrogen, carbon, or a combination thereof. The leaving group can be a chloride, bromide, iodide, or tosylate. The aryl rings of the bismethylene aryl linker compound can be substituted or unsubstituted. When the aryl rings are unsubstituted, the aryl rings do not have any R substituents. When the aryl rings are substituted, each ring independently has 1, 2, 3 or 4 R substituents. The R substituents are halogens, alkyl groups (having from 1 to 15 carbons, including all integer values of carbons and ranges therebetween), alkoxy groups (wherein the alkyl moiety of the alkoxy group has from 1 to 15 carbons, including all integer values of carbons and ranges therebetween), nitro groups, amino groups, alkylamino groups (wherein the alkyl moiety or moieties of the alkylamino group, independently, has from 1 to 15 carbons, including all integer values of carbons and ranges therebetween), trifluoromethyl group or a combination thereof. It is desirable that the aryl structure is symmetrical so that only one isomer (e.g., diastereomer) of the cross-linked peptide is formed due to symmetry-related degeneration.

In another embodiment, the bismethylene aryl linker has the following structure:

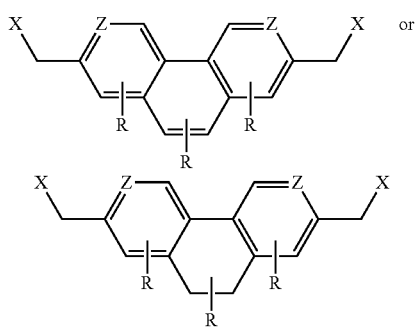

where X and Z are defined above. The aryl rings of this structure can be substituted or unsubstituted as described herein. It is desirable that the structure be symmetrical so that isomers (e.g., diastereomers) of the cross-linked peptide or protein are not formed.

The peptide and bismethylene aryl linker are contacted under conditions (e.g., reaction time, reaction temperature and reaction atmosphere) that result in formation of at least two carbon-sulfur bonds providing at least one cross link as described herein which comprises at least two thioether linkages. Determination of suitable conditions is within the purview of one having skill in the art.

While the cross link can be formed by the reaction as described in the method above, it is considered that the cross link can be formed by reaction of bismethylene aryl linkers with functional groups other than methylene halides described herein, for example, bismethylene aryl tosylates.

In an embodiment, the method of the present invention consists essentially of the steps provided above. In another embodiment, the method of the present invention consists of the steps provided above. In an embodiment, the present invention provides cross-linked peptides made according to the methods described herein.

In another aspect, the present invention provides compositions comprising the cross-linked peptides or proteins of the present invention. The composition can comprise the peptide(s) and other components (e.g., excipients) to form a composition suitable for delivery of the peptide(s) and/or protein(s). For example, the compositions can be in solid form (e.g., a tablet or capsule) or a solution (e.g., an aqueous solution) comprising the peptides or proteins. It is desirable to formulate a composition with long-acting (e.g., controlled release) properties. Such compositions are well-known in the art. In an embodiment, the composition comprises one or more cross-linked peptides or proteins of the present invention and one or more excipients.

Examples of suitable excipients include, but are not limited to, any and all solvents, dispersion media, coatings, antibacterial and antifungal agents, isotonic and absorption delaying agents and the like. The use of such media and agents for formulation of proteins and peptides for delivery applications is well known in the art. Except insofar as any conventional media or agent is incompatible with the active ingredient, its use in the composition is contemplated. Supplementary active ingredients can also be incorporated into the pharmaceutical composition.

The following examples are presented to illustrate the present invention. They are not intended to be limiting in any manner.

Example 1

In order to evaluate the effect of cysteine cross linking on cell permeability, PDI peptide was used as a model peptide because (i) PDI has shown to be an excellent dual inhibitor of the p53-MDM2 and the p53-MDMX interactions, the two validated cancer targets, and (ii) crystal structures of PDI and its analogs in complexes with MDM2 and MDMX have been solved recently. However, PDI was found to be cell impermeable, greatly diminishing its therapeutic potential. Since 12-mer PDI (sequence=LTFEHYWAQLTS SEQ ID NO:1) does not encode cysteine, it was reasonable to believe that two residues at the solvent exposed face of the helix could be replaced with cysteines followed by cysteine-specific cross linking. Inspection of the PDI-MDM2/MDMX complex structures revealed that Glu-4 and Thr-11 are solvent exposed and could be substituted without substantial loss of inhibitory activity, which was confirmed by ELISA (compare 1 to PDI in Table 1). A (D,L)-dicysteine analog 3 was prepared by placing D-Cys at position 4 to investigate configurational effect on the cross-linking reaction. Initial ELISA data indicated that (D,L)-dicysteine substitution was tolerated; in fact, more than 3-fold increase in MDM2 activity was observed (Table 1).

TABLE 1

Sequence and Inhibitory Activity of PDI Analogs[a]

| Name | sequence | charge | MDM2 IC$_{50}$ (nM) | MDMX IC$_{50}$ (nM) |
|---|---|---|---|---|
| PDI[b] | LTFEHYWAQLTS (SEQ ID NO: 1) | −1 | 44 | 500 |
| 1 | LTFCHYWAQLCS (SEQ ID NO: 2) | 0 | 57 ± 4.6 | 1,850 ± 176 |
| 1a | LTFC'HYWAQLC'S[c] (SEQ ID NO: 19) | 0 | 39 ± 3.2 | 4,810 ± 1,120 |
| 1b | LTFC"HYWAQLC"S[d] (SEQ ID NO: 19) | 0 | 35 ± 4.5 | 890 ± 120 |
| 2a | LTFC'RYWARLC'S (SEQ ID NO: 20) | +2 | 244 ± 13 | 5,520 ± 980 |
| 2b | LTFC"RYWARLC"S (SEQ ID NO: 20) | +2 | 237 ± 16 | 1,520 ± 150 |
| 3 | LTFcHYWAQLCS[e] (SEQ ID NO: 4) | 0 | 13 ± 1.3 | 339 ± 27 |
| 3a | LTFc'HYWAQLC'S (SEQ ID NO: 19) | 0 | 8.3 ± 0.5 | 22 ± 4.0 |
| 3b | LTFc"HYWAQLC"S (SEQ ID NO: 19) | 0 | 5.4 ± 0.4 | 14 ± 2.0 |
| 4a | LTFc'RYWARLC'S (SEQ ID NO: 20) | +2 | 208 ± 19 | 4,490 ± 886 |

TABLE 1-continued

Sequence and Inhibitory Activity of PDI Analogs[a]

| Name | sequence | charge | MDM2 IC$_{50}$ (nM) | MDMX IC$_{50}$ (nM) |
|------|----------|--------|---------------------|---------------------|
| 4b | LTFc"RYWARLC"S (SEQ ID NO: 20) | +2 | 102 ± 8.2 | 1,150 ± 87 |

[a] ELISA was repeated three times to derive average IC$_{50}$ values along with standard deviations.
[b] IC$_{50}$ values were taken from ref. 13 where the same assay was performed.
[c] C' denotes the Bph-linked cysteine.
[d] C" denotes the Bpy-linked cysteine.
[e] c (lower case) denotes D-cysteine.

Figure 2:
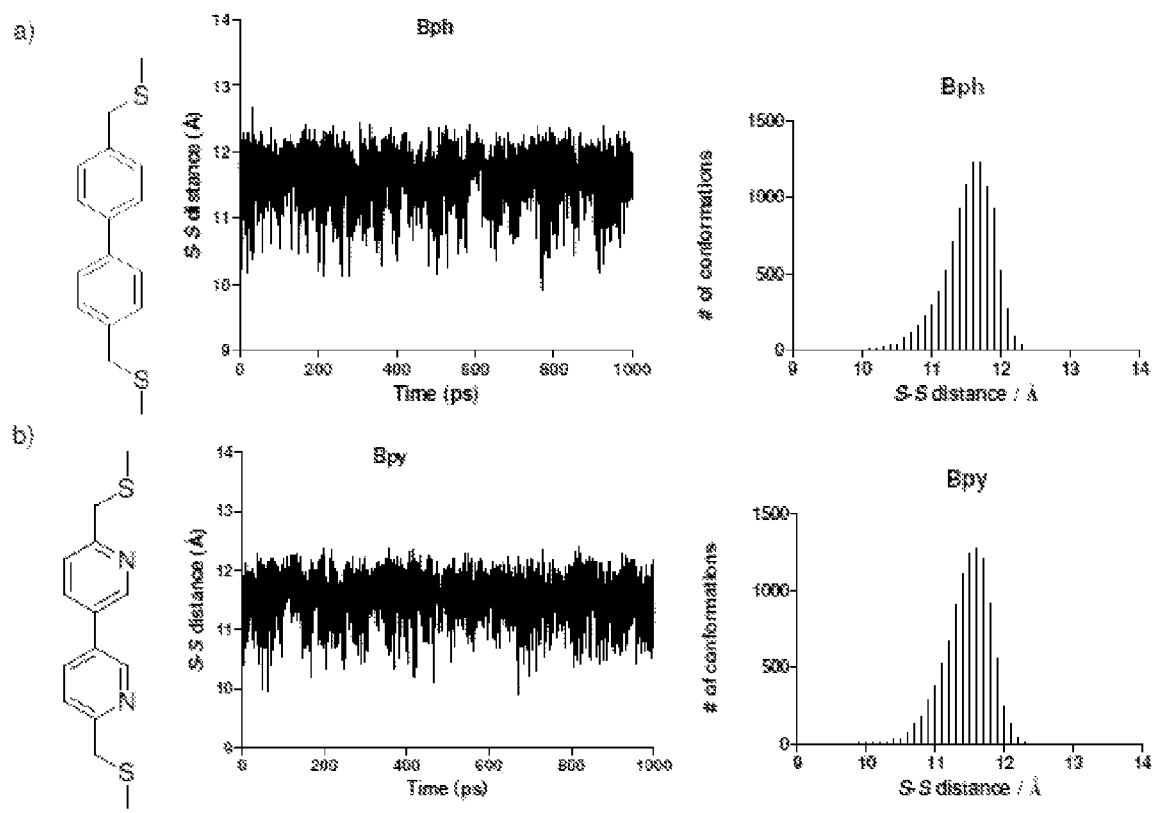
FIG. 2. Distance distributions of S-methyl Bph (a) and Bpy (b) cross linkers calculated using Langevin dynamics simulations.
Figure 3:
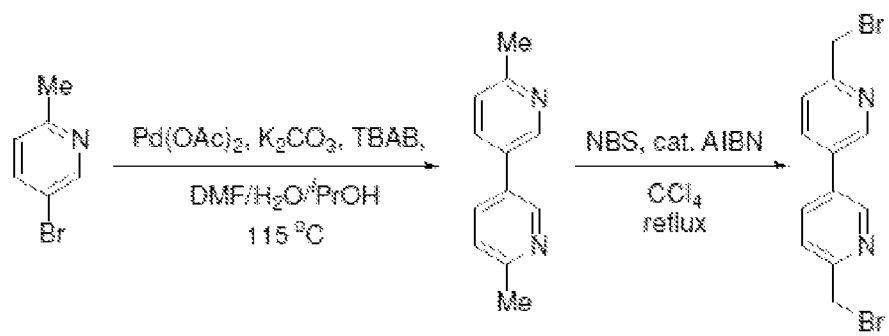
FIG. 3. An example of the synthesis of 6,6'-bis(bromomethyl)-3,3'-bipyridine (Bpy).
Figure 4:
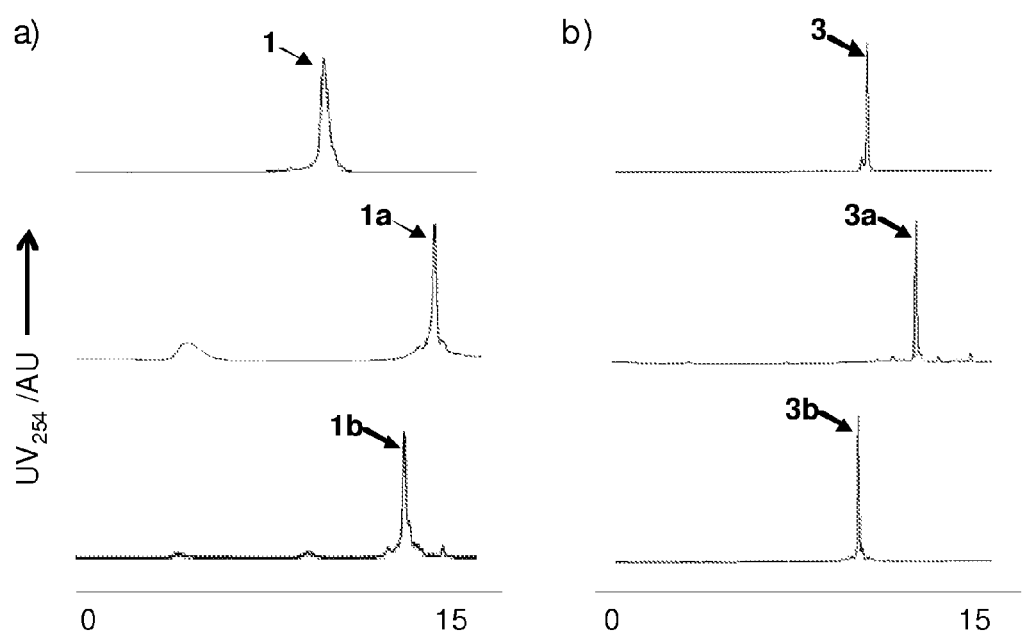
FIG. 4. Examples of HPLC traces of crude products after the cross-linking reaction of PDI analogs 1 (a) and 3 (b) with either Bph or Bpy.

To identify suitable rigid cross linkers that selectively alkylate dicysteines at the i,i+7 positions of PDI with a distance of 11.95 Å between two β-carbons (FIG. 1), various aryl methylene bromides were explored and it was found 4,4'-bis-bromomethyl-biphenyl (Bph) and 6,6'-bis-bromomethyl-[3,3']bipyridine (Bpy) provided nearly perfect matches. In Langevin dynamic simulation study, the median sulfur-to-sulfur distances for the Bph and Bpy scaffolds center around 11.5-11.9 Å (FIG. 2). Importantly, Bph is commercially available while Bpy can be conveniently prepared through a two-step procedure (FIG. 3). Briefly, 6,6'-dimethyl-3,3'-bipyridine was obtained in 51% yield through palladium-catalyzed homo-coupling of 5-bromo-2-methylpyridine under basic condition, which was subsequently transformed into Bpy in 14% isolated yield through direct bromination with 2 equiv NBS in the presence of catalytic amount of AIBN in CCl$_4$. To assess the cysteine cross-linking reaction efficiencies, the fully deprotected peptide 1 or 3 was incubated at a concentration of 1 mM with 1.5 equiv of Bph or Bpy cross linker in a mixed acetonitrile/30 mM NH$_4$HCO$_3$ solvent at pH 8.5. The HPLC traces of the crude products indicated that the reactions proceeded to completion within 2 hours with greater than 95% conversion (FIG. 4). Notably, acyclic dialkylated products (two Bph/Bpy cross linkers added to one peptide) were not detected in the LC-MS analysis, suggesting that cross-linking reaction proceeds much faster than simple double alkylation despite excess amount of Bph and Bpy.

Figure 5:
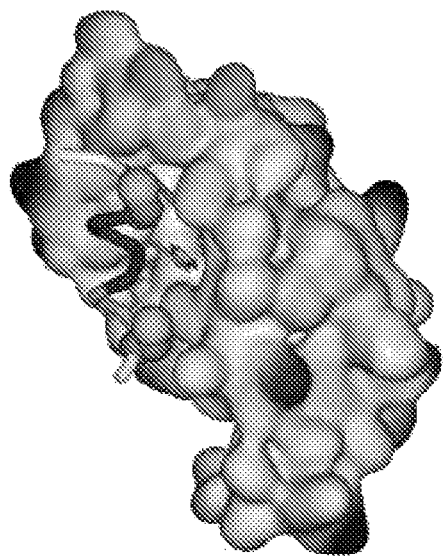
FIG. 5. Possible binding modes of 1 (a), 1b (b), 3 (c), and 3b (d) toward MDMX. The cysteine side chains and the Bpy cross linkers were shown in CPK model and the helical peptides were shown in tube model.
Figure 5:
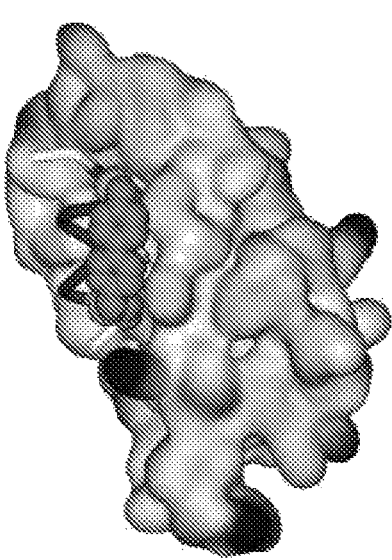
Figure 5:
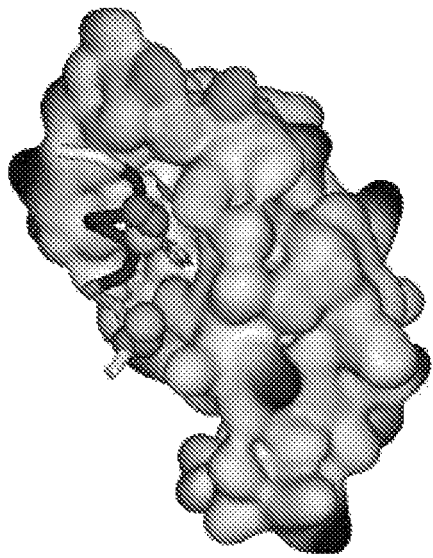
Figure 5:
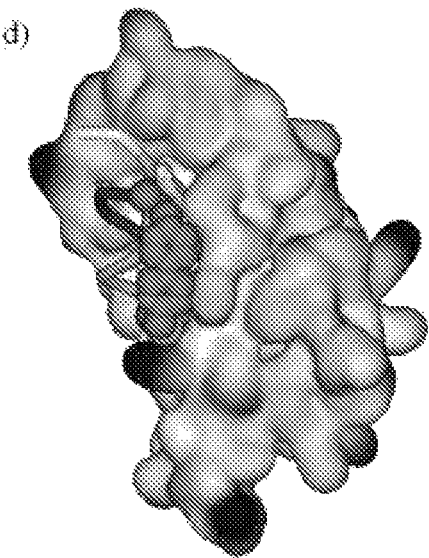

While the initial cross-linked peptides (1a, 1b, 3a, 3b) were charge-neutral, positively charged analogs (2a, 2b, 4a, 4b) were prepared by placing two arginines at the solvent exposed side. Then, ELISA was performed with these compounds to gauge the cross-linking effect on their inhibitory activity (Table 1). All charge-neutral cross-linked peptides showed modest increase in MDM2 activity, but variable effect on MDMX activity relative to their linear counterparts (compare 1a and 1b to 1; 3a and 3b to 3). Interestingly, cysteine cross-linked peptides 3a and 3b with D,L-configuration exhibited a 15- and 24-fold increase in MDMX activity, respectively (Table 1). In a molecular modeling study, the D,L-cysteine-linked Bpy in 3b appears to bind snugly onto a nearby hydrophobic pocket while the L,L-cysteine-linked Bpy does not (FIG. 5). This type of cross-linker-protein surface interaction was observed recently in the crystal structure of Mcl-1 bound to a hydrocarbon cross-linked peptide. Meanwhile, all positively charged peptides showed significantly reduced activities compared to their neutral counterparts (compare 2a to 1a, 2b to 1b, 4a to 3a, and 4b to 3b in Table 1), indicating that arginine substitutions at positions 5 and 9 were not tolerated.

Figure 6:
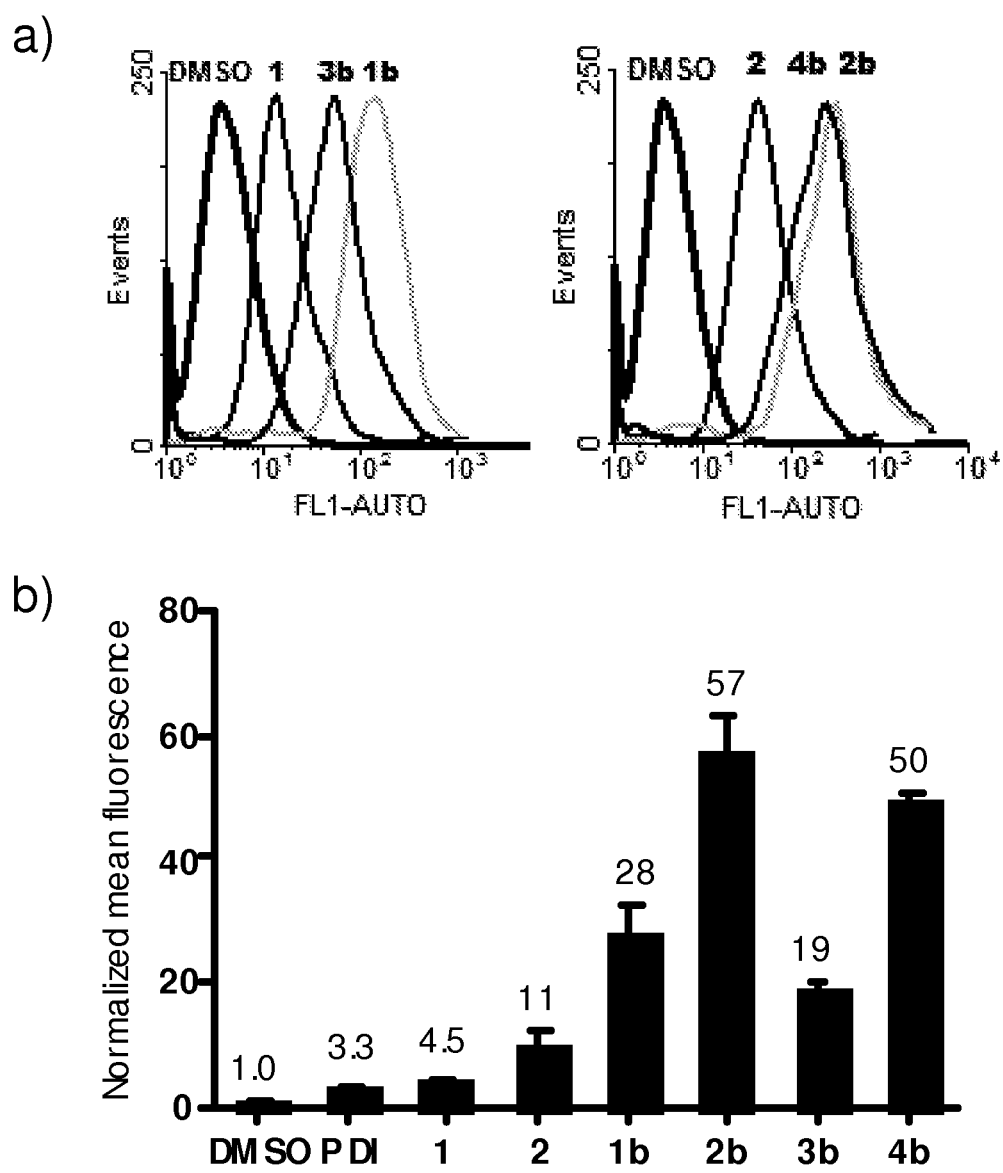
FIG. 6. An example of flow cytometry analysis of HeLa cells after treatment with 10 μM fluorescein-conjugated peptides: (a) Representative histograms; (b) Bar graph showing normalized mean fluorescence.

Next, the effect of cysteine cross linking on cell permeability was examined using fluorescence-activated cell sorting. Because Bpy cross-linked peptides showed improved water solubility and higher bioactivities than Bph cross-linked ones, the N-terminally fluorescein-conjugated 1b, 2b, 3b, and 4b were prepared along with PDI, 1, and 2 as controls. As shown in FIG. 6, linear fluorescein-labeled PDI and 1 exhibited minimal cell penetration relative to the DMSO control. As expected, substituting two arginines into PDI led to 2.5-fold increase in mean fluorescence (compare 2 to 1). However, cysteine cross-linking by Bpy caused a larger increase in mean fluorescence (~6-fold for 1b over 1, ~5-fold for 2b over 2), indicating that the effect of cross linking on cell permeability is greater than that of positive charge. Moreover, these two effects are additive as the positively charged, Bpy cross-linked 2b showed an additional 2-fold increase in permeability compared to 1b. Similar enhancement was observed for peptides 3b and 4b with the D,L-configurations (FIG. 6b).

Figure 7:
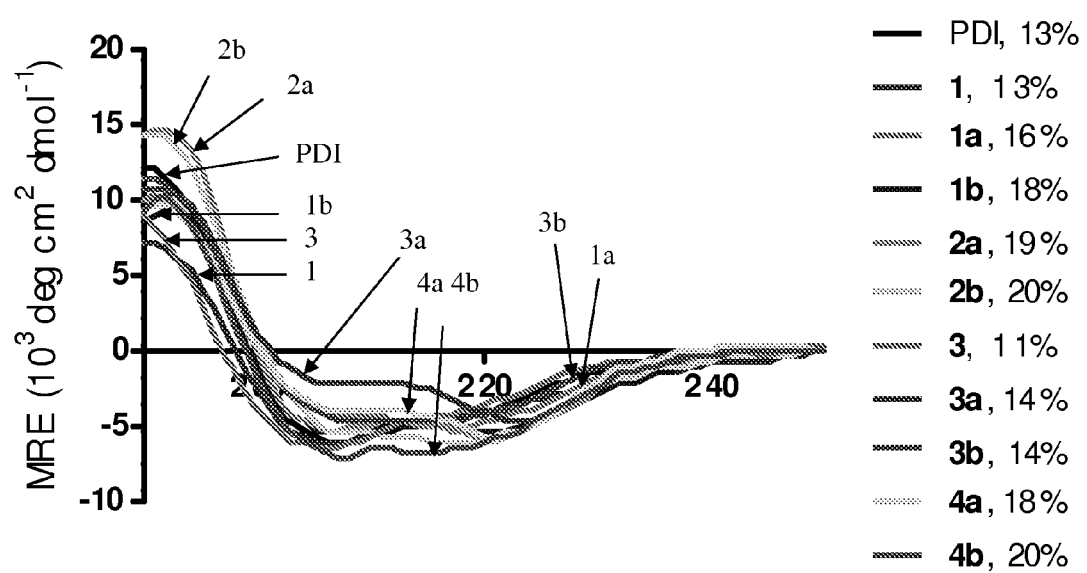
FIG. 7. An example of CD spectra of the linear and cross-linked PDI analogs and their respective percent helicity values: The peptides were dissolved in 20% ACN/H$_2$O for a final concentration of 50 μM. The percent helicity was calculated based on the $[\theta]_{222}$ values.

To determine the extent by which structural change upon cross linking contributes to cell permeability, the CD measurement of all the cross-linked peptides was performed. Compared to the linear 12-mer peptides PDI, 1 and 3 which showed 11-13% helicity, cysteine cross linking caused modest increases in percent helicity (compare 1a/1b to 1, 3a/3b to 3 in FIG. 7). Arginine substitutions led to additional increases (compared 2a/2b to 1a/1b, 4a/4b to 3a/3b), presumably due to higher helix propensity of Arg relative to Glu and Gln (propensity scale: Arg=0.21, Glu=0.40, Gln=0.39). Also, Bpy cross-linked peptides showed slightly higher percent helicity than Bph cross-linked ones. Taken together, a correlation between helicity and permeability appears to exist as peptides with higher helicity generally showed higher cell permeability (compare FIG. 7 to FIG. 6). For positively charged peptides 2b and 4b, other factors such as increased amphiphilicity due to appendage of hydrophobic biaryl groups resulting in an extended hydrophobic face may also play a role in enhancing cell penetration.

Figure 8:
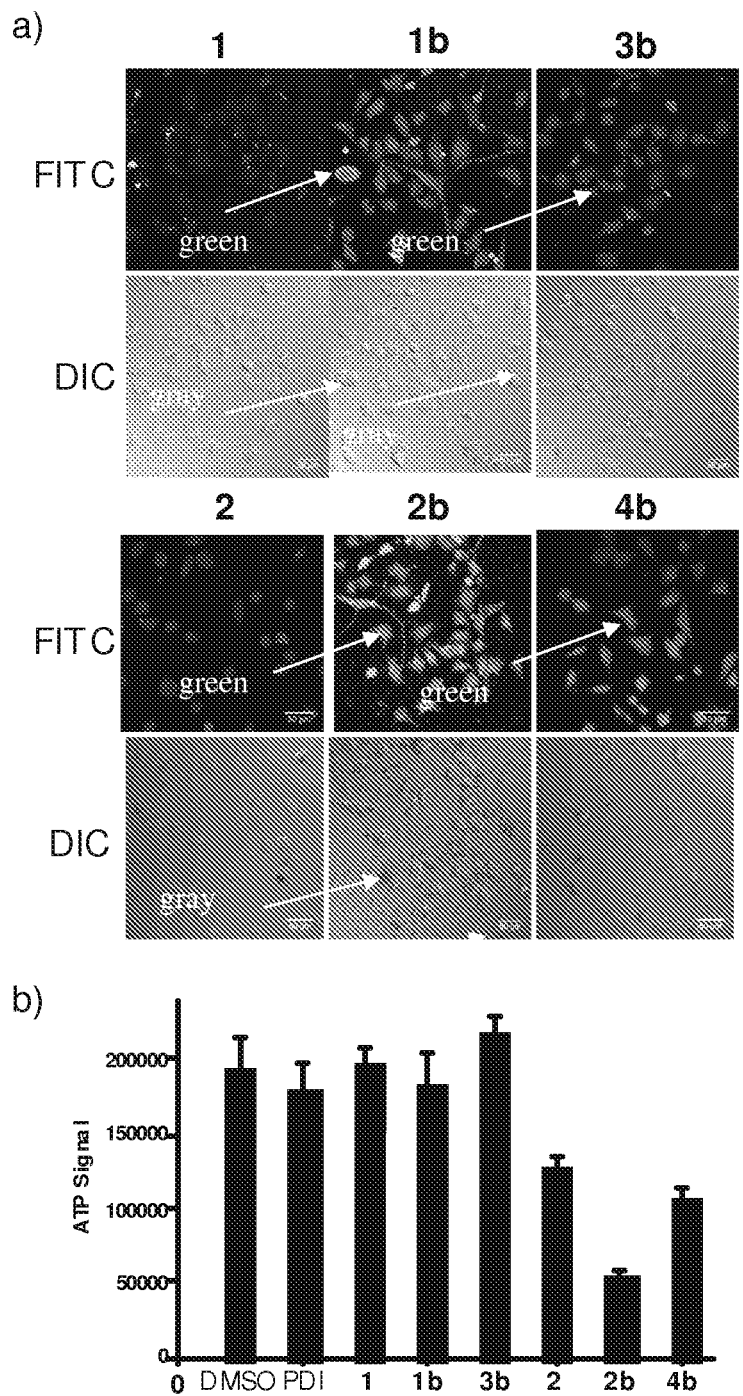
FIG. 8. (a) Confocal images of fixed HeLa cells after treatment with 10 μM of fluorescein-conjugated peptides for 2 hours. Scale bar=50 μm. (b) Cell viability assay using the CellTiter-Glo reagent.
Figure 9:
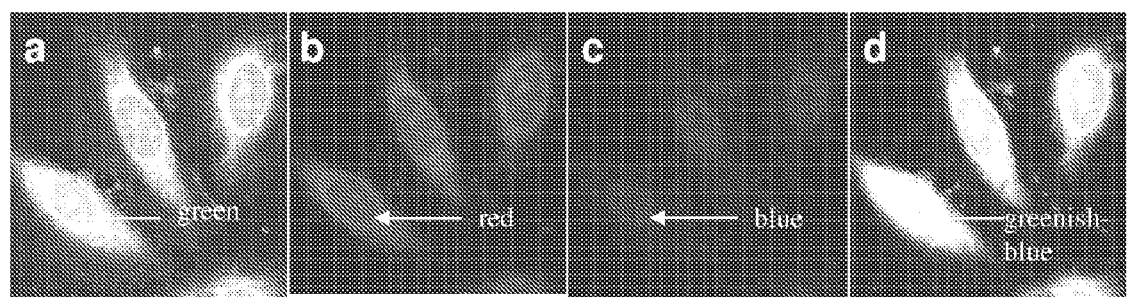
FIG. 9. Confocal fluorescent microscopy of live HeLa cells after treatment with 10 μM of fluorescein-conjugated 3b for 2 hours followed by incubation with 10 μg/mL Alexa Fluor 586 labeled transferrin and 1.5 μM Hoescht 33342 dye for 30 minutes: (a) FITC channel; (b) Fluor 585 channel; (c) Hoescht channel; (d) merged image of channels a-c.

To corroborate the FACS result, a confocal microscopy study was carried out and the data were collected in FIG. 8a. In the FITC channel, the positively charged, Bpy cross-linked peptides 2b and 4b showed the strongest cellular fluorescence, in excellent agreement with the FACS data; however, cellular debris was detected for 2b and 4b treated cells in the DIC channel, indicating apparent cytotoxicity. This cytotoxicity was further confirmed by the ATP assay (FIG. 8b), which was attributed to the positive charge as the Bpy cross-linked charge-neutral 1b and 3b did not show any cytotoxicity (FIGS. 8a and 8b). To gain an insight into possible mechanism of cell permeation, the subcellular localization of 3b, the most potent, permeable, non-toxic peptide in our series, was examined in live HeLa cells by confocal microscopy after treatment with 3b, followed by Alexa Fluor 647 labeled transferrin and Hoescht 33342 to visualize the recycling endosomes and nuclei, respectively (FIG. 9). It was found while 3b showed a more diffusive distribution in the cytosol (panel a), it predominantly co-localized with transferrin in the recycling endosomes (panels b and d), suggesting that a likely mode of cell penetration for 3b is via the endosome-mediated active transport.

Materials and General Procedures. 4,4'-Bis-bromomethyl-biphenyl (Bph) was purchased from TCI America and used directly in the crosslinking reactions. All other chemicals and solvents were obtained from commercial sources and used without further purification. Analytical thin layer chromatography (TLC) was performed on Whatman AL SIL G/UV254 flexible plates. Flash chromatography was performed with SiliCycle silica gel 60 Å (40-63 μm). All reactions were carried out under argon using oven-dried glassware. $^1$H— and $^{13}$C-NMR spectra were recorded with either Inova-500 or Gemini-300 MHz NMR spectrometers. Electrospray LCMS analysis was performed using a Finnigan LCQ Advantage IonTrap mass spectrometry coupled with a Surveyor HPLC system. Peptides were purified using a Gilson semi-preparative reverse-phase HPLC system equipped with a Phenomenex $C_{18}$ column with a flow rate of 5 mL/min and a gradient of 10-90% ACN/$H_2O$ while monitoring at 220 nm and 254 nm. Analytical HPLC were performed using Phenomenex Luna $C_{18}$ or Kinetex $C_{18}$ column (250×4.6 mm) with the flow rate at 1.0 mL/min and UV detection set at 220 and 254 nm. Live cell microscopy was performed on a Zeiss LSM-510 meta-NLO system equipped with a Coherent Chameleon Ultra II Ti/Sapphire laser and external non-descanned detectors. Fixed cell fluorescent microscopy was performed on a Zeiss LSM-710 Confocal Microscope equipped with a continuous laser and fluorescence lifetime (FLIM) detectors. For Table 2, the following SEQ ID NOs apply: PD1 is SEQ ID NO:1; 1 is SEQ ID NO: 2; 1a and 1b are SEQ ID NO:19, 2 is SEQ ID NO:3; 2a and 2b are SEQ ID NO:20; 3 is SEQ ID NO:4; 3a and 3b are SEQ ID NO:29; 4a and 4b are SEQ ID NO:20; Fluo-1 is SEQ ID NO:1; Fluo-1 is SEQ ID NO:2; Fluo 1b is SEQ ID NO:19; Fuo-2 is SEQ ID NO:3; Fluo-2b is SEQ ID NO:20; Fluo-3b is SEQ ID NO:19; and Fluo-4-b is SEQ ID NO:20.

TABLE 2

ESI-MS Characterization of PDI analogs.

| Peptide | Sequence | Mass calculated ($M^+$, m/z) | Mass found (m/z) |
|---|---|---|---|
| PDI | LTFEHYWAQLTS | 1536.7 | 1536.6 [M + H]$^+$ |
| 1 | LTFCHYWAQLCS | 1512.7 | 1513.2 [M + H]$^+$ |
| 1a | LTFC'HYWAQLC'S$^a$ | 1690.8 | 1691.5 [M + H]$^+$ |
| 1b | LTFC"HYWAQLC"S$^b$ | 1692.6 | 1693.2 [M + H]$^+$ |
| 2 | LTFCRYWARLCS | 1559.8 | 1560.2 [M + H]$^+$ |
| 2a | LTFC'RYWARLC'S | 1736.8 | 1737.5 [M + H]$^+$ |
| 2b | LTFC"RYWARLC"S | 1738.8 | 1739.4 [M + H]$^+$ |
| 3 | LTFcRYWARLCS | 1512.7 | 1513.5 [M + H]$^+$ |
| 3a | LTFc'RYWARLC'S | 1690.8 | 1691.4 [M + H]$^+$ |
| 3b | LTFc"RYWARLC"S | 1692.6 | 1693.5 [M + H]$^+$ |
| 4a | LTFc'RYWARLC'S | 1736.8 | 1737.2 [M + H]$^+$ |
| 4b | LTFc"RYWARLC"S | 1738.8 | 1739.9 [M + H]$^+$ |
| Fluo-PDI | Fluorescein-Ahx-LTFEHYWAQLTS$^d$ | 1995.6 | 998.5 [M + 2H]$^{2+}$ |
| Fluo-I | Fluorescein-Ahx-LTFCHYWAQLCS | 1971.7 | 987.4 [M + 2H]$^{2+}$ |
| Fluo-1b | Fluorescein-Ahx-LTFC"HYWAQLC"S | 2151.0 | 1076.9 [M + 2H]$^{2+}$ |
| Fluo-2 | Fluorescein-Ahx-LTFCRYWARLCS | 2018.8 | 1010.5 [M + 2H]$^{2+}$ |
| Fluo-2b | Fluorescein-Ahx-LTFC"RYWARLC"S | 2198.0 | 1100.2 [M + 2H]$^{2+}$ |
| Fluo-3b | Fluorescein-Ahx-LTFc"RYWARLC"S | 2151.0 | 1076.2 [M + 2H]$^{2+}$ |
| Fluo-4b | Fluorescein-Ahx-LTFc"RYWARLC"S | 2198.0 | 1110.8 [M + 2H]$^{2+}$ |

$^a$C' denotes the Bph-linked cysteine;
$^b$C" denotes the Bpy-linked cysteine;
$^c$c (lower case) = D-cysteine.
$^d$Ahx = 6-aminohexanoic acid.

6,6'-Dimethyl-3,3'-bipyridine: A mixture of 5-bromo-2-methyl-pyridine (1.37 g, 8 mmol), Pd(OAc)$_2$ (90 mg, 0.4 mmol), $K_2CO_3$ (1.10 g, 8 mmol), tetra-n-butylammonium bromide (1.29 g, 4 mmol) in DMF (0.9 mL)/$H_2O$ (0.35 mL) was stirred at 115° C. under argon for 2 minutes. Isopropanol (480 mg, 8 mmol) was added. After stirring for 48 h, the reaction mixture was allowed to cool down to room temperature. The mixture was added water and ether, and the organic phase was separated, washed with brine, and dried over anhydrous $Na_2SO_4$. The solvent was then evaporated under reduced pressure and the residue was purified by silica gel column chromatography to afford the desired product as white crystals (0.377 g, 51%): $^1$H NMR (500 MHz, $C_6D_6$) δ 8.71 (d, J=1.5 Hz, 2H), 7.18 (dd, J=8.0 Hz, 2.5 Hz, 2H), 6.66 (d, J=8.0 Hz, 2H), 2.45 (s, 6H).

6,6'-Bis(bromomethyl)-3,3'-bipyridine (Bpy): 6,6'-dimethyl-3,3'-bipyridine (0.368 g, 2 mmol) was dissolved in 20 mL anhydrous $CCl_4$. N-bromosuccinimide (0.712 g, 4 mmol) and AIBN (20 mg, catalytic amount) were added to the solution. The mixture was refluxed for 5 hours before $CCl_4$ was removed under vacuum. Recrystallization of the crude from DCM afforded the titled compound as a white solid (90 mg, 14% yield): $^1$H NMR (300 MHz, $CDCl_3$) δ 8.80 (d, J=2.1 Hz, 2H), 7.89 (dd, J=8.1 Hz, 2.4 Hz, 2H), 7.56 (d, J=8.1 Hz, 1H), 4.61 (s, 4H); $^{13}$C NMR (75 MHz, $CDCl_3$) δ 156.76, 147.96, 135.44, 132.26, 123.62, 33.29; HRMS (EI) calcd for $C_{12}H_{10}Br_2N_2$ 339.9205 [M$^+$]. found 339.9206.

Langevin Dynamics. The distance distributions of Bph and Bpy cross linkers were calculated using Langevin dynamics simulations. The S-methylated cross linkers were used in this simulation and their structures were shown on the top. The distance between the two sulfur atoms was monitored throughout the simulation. The langevin dynamics simulation was carried out with Hyperchem 8.0. The structures were minimized using Amber 99 force field prior to dynamics simulation. The simulation was set up to last 1000 ps with 1-ps timestep at 300 K. A unimodal distribution was observed when the number of conformations was plotted to the S-S distance. The median S-S distances for both cross linkers stand around 11.5-11.9 Å.

Solid Phase Peptide Synthesis. The linear peptides were synthesized by following the standard Fmoc peptide synthesis protocol with Rink amide resin (substitution=0.66 mmol/g) on a Tribute peptide synthesizer (Protein Technologies, Tuson, Ariz.). For each coupling reaction, 5 equiv of Fmoc-amino acid, 5 equiv of HBTU, and 10 equiv of N-methylmorpholine (NMP) were used. The coupling reaction was allowed to proceed for 45 minutes. For coupling of cysteine, 1 M of trimethylpyridine in DCM/DMF (1:1) was employed along with a reduced preactivation time (0.5 minute) in order to minimize racemization. The Fmoc deprotection was accomplished by treating the peptide-bound resin with 20% piperidine/DMF (3×, 8 minutes each). After the amino acids were assembled, the N-terminal amine was acylated using 10 equiv of acetic anhydride and 10 equiv of DIEA. The peptides were then cleaved by treating the resin with a cleavage cocktail containing 95% TFA, 2.5% ethane dithiol, 1.5% triisopropylsilane and 1% water for a period of 1.5 hours (extended to 2.5 hours for peptides containing Pbf protecting groups). The peptides were precipitated in diethyl ether, collected by centrifugation, and washed with diethyl ether prior to drying in high vacuum. The crude peptides were purified by Gilson reverse-phase HPLC equipped with a semi-prep Phenomenex C18 column running at a flow rate of 5 mL/min and a gradient of 10-90% acetonitrile/$H_2O$ containing 0.1% TFA. Fractions with greater than 90% purity were pooled and lypholized to give the desired peptides. For the synthesis of fluorescein-labeled peptides, chain elongation was allowed to continue with Fmoc-Ahx-OH. After removal of Fmoc, the N-terminus of the peptide was capped by incubating the peptide with 1.5 equiv of FITC overnight in presence of 2 equiv of DIEA.

Peptide Cross-Linking by Bph or Bpy. Cross-linking reactions were carried out by incubating the purified dicysteine-containing peptides with 1.5 equiv of 4,4'-bis(bromomethyl)-1,1'-bipheny (Bph, a) or 6,6'-bis(bromomethyl)-3,3'-bipyridine (Bpy, b) in a mixed solvent of acetonitrile/30 mM $NH_4HCO_3$ buffer, pH 8.5 (1:4 to 2:3 depending on peptide solubility) to obtain a final peptide concentration of 1 mM. The mixture was stirred at room temperature for 1.5-2 hrs. Afterwards, the solvents were evaporated and excess amount of cross linker was removed by washing the residue with diethyl ether. The cross-linked peptides were then purified by preparative HPLC, and their identities were confirmed by electrospray mass spectrometry (Table 2).

Figure 10:
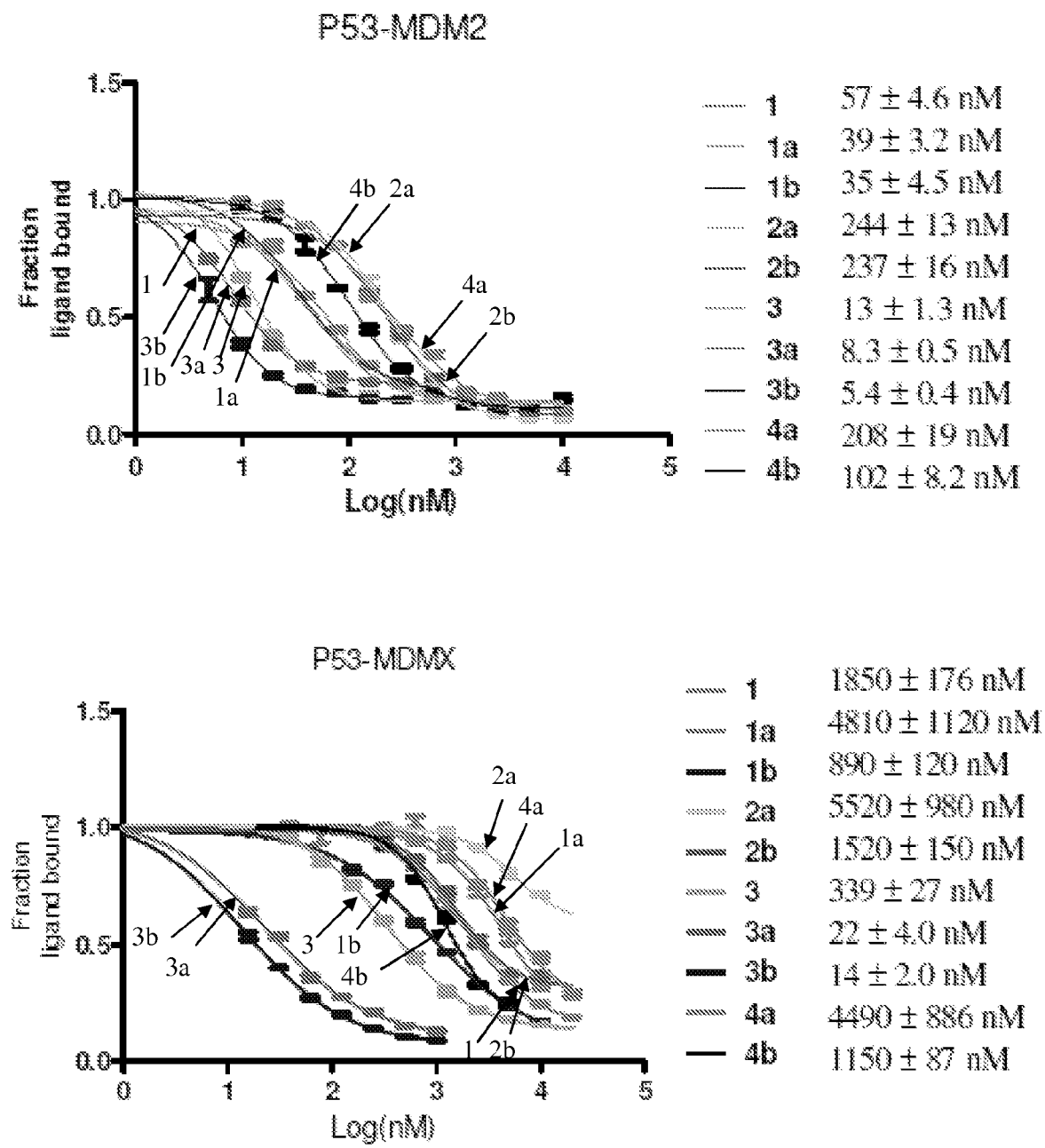
FIG. 10. ELISA data of the cross-linked PDI analogs. The experiments were repeated three times and the resulting data were plotted with GraphPad Prism 5.0 to derive the average IC$_{50}$ values along with standard deviations.

ELISA Assay. GST-MDM2 and GST-MDMX containing full-length human MDM2 and MDMX and His$_6$-tagged human p53 were expressed in *Escherichia coli* and purified by glutathione agarose and Ni$^{2+}$-nitrilotriacetic acid beads, respectively, under non-denaturing conditions. Microtiter plates were coated with 2.5 µg/ml His$_6$-p53 in PBS buffer for 16 hours. After washing with PBS containing 0.1% Tween-20 (PBST), the plates were blocked with PBST containing 5% nonfat dry milk (PBSTM) for 30 minutes. Peptides were dissolved in DMSO. GST-MDM2 and MDMX (5 µg/ml) were mixed with peptides in PBSMT containing 10% glycerol and 10 mM dithiolthreitol prior to their additions to the wells at the specified concentrations. The incubation was allowed to proceed for 1 hour at room temperature before the plates were washed with PBST. The plates were then incubated with either anti-MDM2 antibody 5B10 or anti-MDMX antibody 8C6 in PBSTM for 1 hours, followed by washing with PBST and incubation with horseradish peroxidase-conjugated rabbit anti-mouse Ig antibody for 1 hour. The plates were developed by incubation with TMB peroxidase substrate (KPL, Gaithersburg, Md.) and measured by absorbance at 450 nm. The data was analyzed with the Origin 6.0 software. ELISA data was normalized such that % ligand bound at infinite dilution of inhibitor was taken to be 100%. Plotting of the data was % ligand bound vs. log of the concentration of inhibitor to yield a sigmodial plot. The sigmodial plot was then fitted to the Hill equation for one site competitive binding mode to derive $IC_{50}$ values. The $IC_{50}$ values were reported as a mean and standard deviation of three independent experiments (FIG. 10).

Molecular Modeling Studies of 3b. The coordinates for PDI complexed with MDMX was obtained from the PDB Code: 3FDO. Two L-Cys substitutions were introduced to replace Glu-4 and Thr-11 of PDI and the resulting peptide 1 was energy-minimized using the Amber 99 force field in Hyperchem 8 to produce a model of MDMX-bound 1 (a). Similarly, L-cys at position 4 of peptide 1 was replaced with Dcys, and the resulting peptide 3 was energy-minimized to generate MDM-bound 3 (c). Separately, Bpy cross linker was constructed and energy-minimized initially before connecting to sulfhydryl groups of the cysteines to generate peptides 1b and 3b. Then, the cross-linked peptide-MDMX complexes were subjected to complete energy minimization in Hyperchem 8. The optimized complex structural models were shown in (b) and (d).

FACS Analysis. HeLa Cells were cultured in DMEM medium supplemented with 10% fetal bovine serum in 6-well plate in a 37° C., 5% $CO_2$ incubator to reach confluency of around 70%. The cells were then washed twice with PBS before switching to serum-free DMEM medium. After standing in the incubator for 30 minutes, appropriate amounts of peptides (1 mM in DMSO) were added to the culture plate to obtain a final peptide concentration of 10 µM. Cells were incubated at 37° C. for additional 2 hrs. Then the medium was removed and the cells were washed with PBS (3×) followed by treatment with trypsin to detach the cells. After a brief low-speed centrifugation, the HeLa cells were collected and re-suspended in PBS for the FACS analysis.

Circular Dichroism Study. Circular dichroism spectra were recorded on JASCO J-715 CD spectrometer at room temperature using 0.1-cm path length cuvette. The spectra were recorded in the wavelength range of 190-250 nm and averaged over 3 scans with a resolution of 0.5 nm, a bandwidth of 1.0 nm and a response time of 4 s. The sensitivity and the speed of the spectrometer were set to 100 mdeg and 50 nm/min, respectively. All peptides were dissolved in 20% acetonitrile/$H_2O$ to reach final concentration of 50 µM. The mean residue ellipticity was plotted to wavelength, and the helical content of each peptide at 222 nm was derived. The percent helicity was calculated based on $[\theta]_{222}/[\theta]max$. $[\theta]max$ was calculated to be −30384 according to the formula: $[\theta]max=−39500×(1−3/n)$ where n is number of bonds.

Confocal Microscopy

HeLa Cells were seeded into 35 mm glass bottom microwell dishes (MatTek, Ashland, Mass.) at a density of 3×105 in DMEM medium supplemented with 10% fetal bovine serum, and the cells were allowed to grow in a 37° C. 5% $CO_2$ incubator for 48 hours. After removing medium, the cells were washed twice with PBS and then incubated in serum-free DMEM medium for 30 minutes. Appropriate amounts of peptides (1 mM in DMSO) were then added to obtain a final concentration of 10 µM and cells were incubated at 37° C. for 2 hours. After PBS wash, cells were treated with 4% formaldehyde in PBS for 20 minutes at room temperature. The fixation medium was removed and the cells were washed with PBS (3×) before placing cells into the low florescent mounting medium for fluorescent imaging acquisition.

Live Cell Confocal Microscopy. HeLa cells were cultured in a 35-mm glass bottom microwell dish as described previously. The cells were incubated with peptide 3b for 2 hrs in a serum-free medium followed by addition of a 40 µL solution containing 500 µg/mL of Alexa Fluor 586-labeled transferring (Invitrogen, Carlsbad, Calif.) and 1.5 µM Hoescht 33342 dye and additional incubation for 30 minutes. Afterwards, cells were washed with PBS and placed into the Earle's balanced salt solution supplemented with MEM essential and non-essential amino acids. All images were taken with a Zeiss LSM-510 meta-NLO system equipped with a Coherent Chameleon Ultra II Ti/Sapphire laser and external non-descanned detectors.

Cell Viability Assay. HeLa cells were seeded into an opaque 96-well plate at a density of $1×10^4$ per well in 100 µL DMEM medium supplemented with 10% FBS and the cells were allowed to grow in a 37° C. 5% $CO_2$ incubator for 48 hrs to reach confluency of around 80%. Prior to the compound treatment, the medium was replaced with serum-free medium and the cells were incubated for 30 minutes. Appropriate amounts of peptides (1 mM in DMSO) were then added to obtain a final concentration of 10 µM and the cells were incubated at 37° C. for 2 hours. Afterwards, the plate was allowed to stand at room temperature for 30 minutes before 100 µL of Cell-Titer Glow reagent (Promega) was added. The plate was incubated at room temperature for 10 minutes. The luminescence signals were recorded with an FLX 800 luminescence plate reader (BioTek). The plotted data represented the average of the readings from 4 separate wells.

Example 2

Among the eight BH3-only proteins (Bim, Puma, Bmf, Bad, Bik, Hrk, Bid and Noxa), only Noxa shows selective interaction with Mcl-1. In a competitive binding assay with the immobilized mouse BimBH3-(83-108) peptide, human NoxaBH3-(18-43) showed $IC_{50}$ values of 24 nM against Mcl-1, 180 nM against Bfl-1/A1, and >100 µM against Bcl-2, Bcl-xL and Bcl-w. Similarly, BH3 peptides derived from mouse Noxa, NoxaA-(16-41) and NoxaB-(68-93), bind to Mcl-1 selectively with $IC_{50}$ values of 87 nM and 109 nM, respectively. Notably, NoxaBH3 peptide augments the effect of Bcl-2/Bcl-xL/Bcl-w-specific BadBH3 in inducing apoptosis in mouse embryonic fibroblasts (MEFs), suggesting that it might be useful in a combination therapy with known small-molecule Bcl-2 inhibitors such as ABT-737. Among the three Noxa BH3 peptides, human Noxa and mouse NoxaA bind to both Mcl-1 and A1, but mouse NoxaB binds only to Mcl-1 with $K_D$ of 126 nM as determined by isothermal titration calorimetry at 25° C. All three structures of the Noxa BH3 peptides in complexes with Mcl-1 showed a nearly identical binding mode in which Noxa helix fits snugly into the Mcl-1 hydrophobic groove. Compared to other Bcl-2 family proteins such as Bcl-xL, Mcl-1 exhibits a more constricted and discontinuous binding surface and minimal conformational change upon binding of BH3 peptides, which may explain the difficulty in identifying potent Mcl-1-selective small-molecule inhibitors. Based on these observations, we decided to use NoxaB BH3 peptide as a template to design our cross-linked peptide-based Mcl-1 inhibitors.

Since NoxaB-(75-93)-C75A peptide retains the activity of full-length NoxaB peptide, we designed the cross-linked NoxaBH3 peptides based on this 19-mer peptide. Since bisaryl cross linkers Bph and Bpy work efficiently with helical peptides containing cysteines at the i,i+7 positions, two solvent-exposed sites in NoxaB peptide, Gln-77/Lys-84 and Arg-80/Leu-87, were selected for substitutions with either D- or L-cysteine followed by the cysteine-based cross linking. The inhibitory activities of the resulting cross-linked BH3 peptides (Table 5) were then evaluated by fluorescence polarization assay (FPA) and ELISA (Table 3).

TABLE 3

Sequence and Inhibitory Activity of the Cross-Linked Noxa Peptides

| Peptide | Sequence | FP, $IC_{50}$ (nM)[a] | ELISA, $IC_{50}$ (nM) |
|---|---|---|---|
| NoxaB[75-93]-C75A | AAQLRRIGDKVNLRQKLLN (SEQ ID NO: 15) | 1,200 ± 240 | 340 |
| 5a | AAC'LRRIGDC'VNLRQKLLN[b] (SEQ ID NO: 16) | 18 ± 6 | 75 |
| 5b | AAC"LRRIGDC"VNLRQKLLN[c] (SEQ ID NO: 16) | 45 ± 9 | 25 |
| 6a | AAc'LRRIGDC'VNLRQKLLN[d] (SEQ ID NO: 16) | 73 ± 18 | 260 |
| 6b | AAc"LRRIGDC"VNLRQKLLN[e] (SEQ ID NO: 16) | 140 ± 43 | 140 |
| 7a | AAQLRC'IGDKVNC'RQKLLN (SEQ ID NO: 17) | 32 ± 5 | 37 |
| 8a | AAC'$_m$LRRIGDC'$_m$VNLRQKLLN[f] (SEQ ID NO: 16) | 230 ± 130 | ND |

[a]FP assay was repeated three times and average $IC_{50}$ values were derived along with their standard deviations.
[b]C' denotes the Bph-linked L-cysteine.
[c]C" denotes the Bpy-linked L-cysteine.
[d]c' (lower case) denotes the Bph-linked D-cysteine.
[e]c" (lower case) denotes the Bpy-linked D-cysteine.
[f]C'$_m$ denotes the Bph-linked α-methyl-L-cysteine.

Compared to the parent linear peptide, the Bph-cross-linked peptides 5a and 6a showed 67-fold and 37-fold increase in activity, respectively, in FPA. The three most potent cross-linked peptides in FPA, 5a, 5b and 6a, also showed potent activities in ELISA with $IC_{50}$ values in the range of 25-75 nM, up to 14-fold improvement over the parent peptide. To determine the selectivity of Mcl-1 inhibitors, N-terminal fluorescein-labeled cross-linked peptides 5a and 6a were prepared and their binding affinities toward Mcl-1 and Bcl-xL were measured by FP assay. Gratifyingly, the cross-linked peptides showed sub-nanomolar affinity toward Mcl-1 but no measurable affinity toward Bcl-xL, indicating a greater than 2.000-fold selectivity (Table 4). By contrast, Bim showed almost equal potency toward Mcl-1 and Bcl-xL.

TABLE 4

Binding Affinity of the Cross-Linked Noxa Peptides

| Peptide | GST-Mcl-1 $K_d$ (nM) | GST-Bcl-xL $K_d$ (nM) |
|---|---|---|
| Bim | 2.5 ± 0.4 | 1.4 ± 0.2 |
| Bak | 127 ± 20 | 14 ± 1 |
| Fl-NoxaB$^{75-93}$-C75A | 2.1 ± 0.2 | >2,000 |
| Fl-5a | 0.8 ± 0.1 | >2,000 |
| Fl-6a | 0.7 ± 0.1 | >2,000 |

Figure 11:
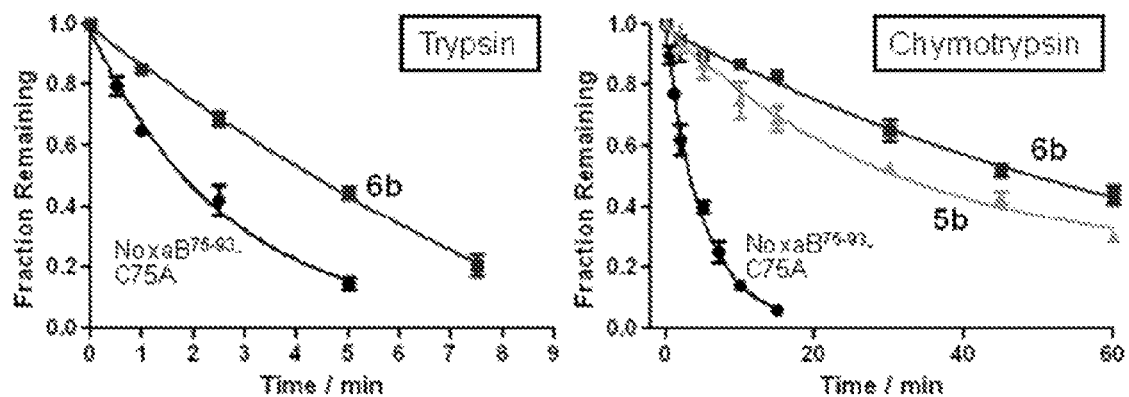
FIG. 11. Proteolytic stability of the linear and stapled Noxa peptides against trypsin (Type IX-S, 13,000-20,000 unit/mg, Sigma) and chymotrypsin (Type II, 40 unit/mg, Sigma). To a solution of 400 μL of 0.25 mM peptide in NH$_4$HCO$_3$ buffer, pH 8.0, was added 80 μL trypsin (5 μg/mL) or chymotrypsin (25 μg/mL), and the resulting solution was incubated at 37° C. At the indicated times, 40 μL of the solution was transferred to 40 μL trifluoroacetic acid to quench the reaction. The samples were analyzed by reverse-phase HPLC using benzophenone as an injection control.

Furthermore, in the trypsin-mediated proteolytic stability assay, Bpy-cross-linked 6b (selected for better water solubility) exhibited $t_{1/2}$ of 11.5 minutes compared to 1.8 minutes for the parent peptide, whereas in the chymotrypsin assay cross-linked peptides 5b and 6b exhibited $t_{1/2}$ of 22 minutes and 54 minutes, respectively, vs. 3.3 minutes for their parent peptide. Taken together, Bpy stapling led to increased proteolytic stability, with 6b being >6 times more stable against trypsin and >16 times more stable against chymotrypsin than its parent linear peptide (FIG. 11).

Figure 12:
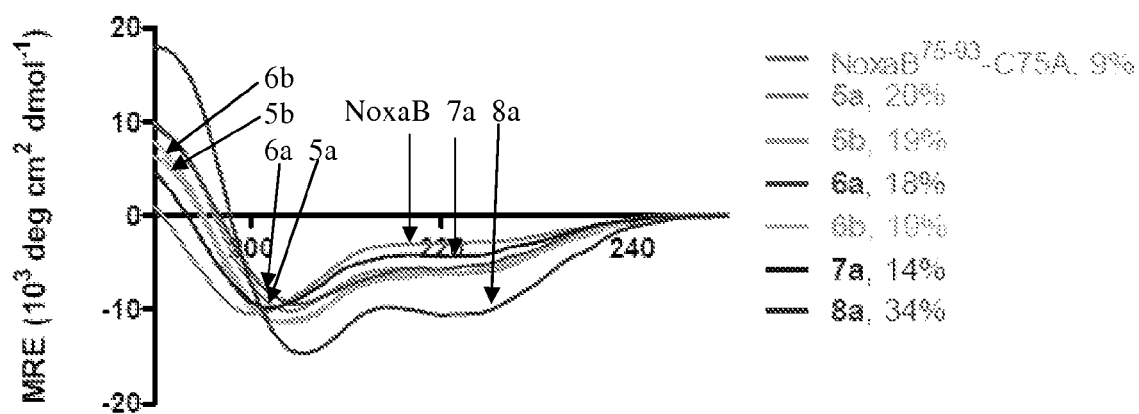
FIG. 12. CD spectra of the linear and cross-linked Noxa peptides and their respective percent helicity values. The peptides were dissolved in 20% ACN/H$_2$O for a final concentration of 50 μM. The percent helicity was calculated based on the $[\theta]_{222}$ values.

To evaluate the effect of cross linking on the alpha-helicity of the Noxa peptides, CD measurement was carried out. Significant increases in percent helicity were observed after cross linking (FIG. 12). Cross-linked peptides 5a, 5b, 6a, and 6b showed roughly 2-fold enhancement compared to the linear NoxaBH3 peptide. Interestingly, when we used α-methyl-L-cysteines in place of cysteines to afford the cross-linked peptide 8a, nearly 3-fold increase in percent helicity was observed compared to the linear NoxaBH3 peptide (FIG. 12).

Figure 13:
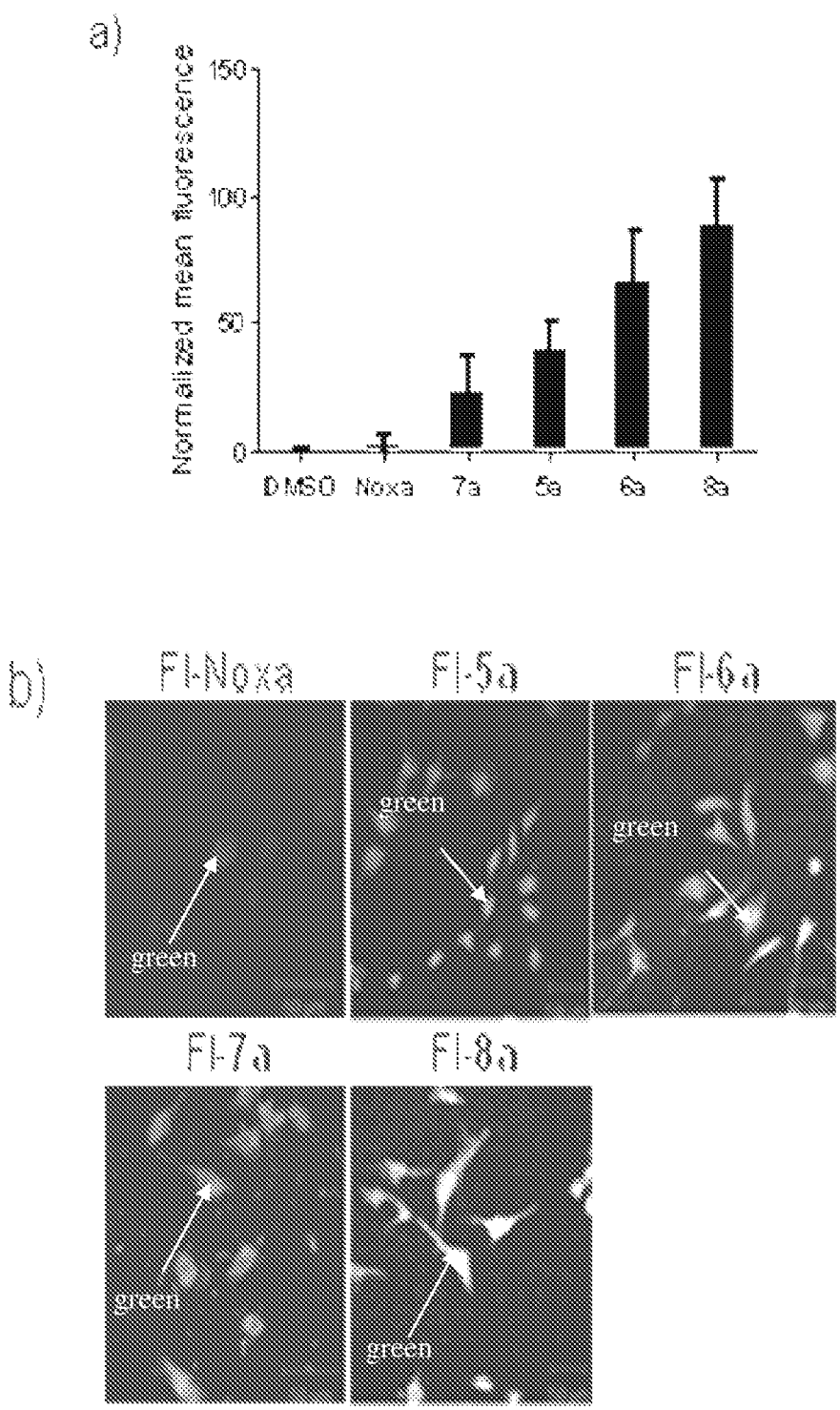
FIG. 13. Cross-linked NoxaB-BH3 peptides showed improved cellular uptake in HeLa cells. (a) Flow cytometry analysis of cell permeability of the FITC-labeled linear or stapled peptide. HeLa cells were treated with 10 μM of fluorescein-labeled peptides in serum-free DMEM medium for 2 hours followed by fixation with formaldehyde. (b) Fluorescent micrographs of HeLa cells treated with 10 μM of fluorescein-labeled (Fl) linear or cross-linked NoxaBH3 peptide. Scale bar=50 μm.
Figure 14:
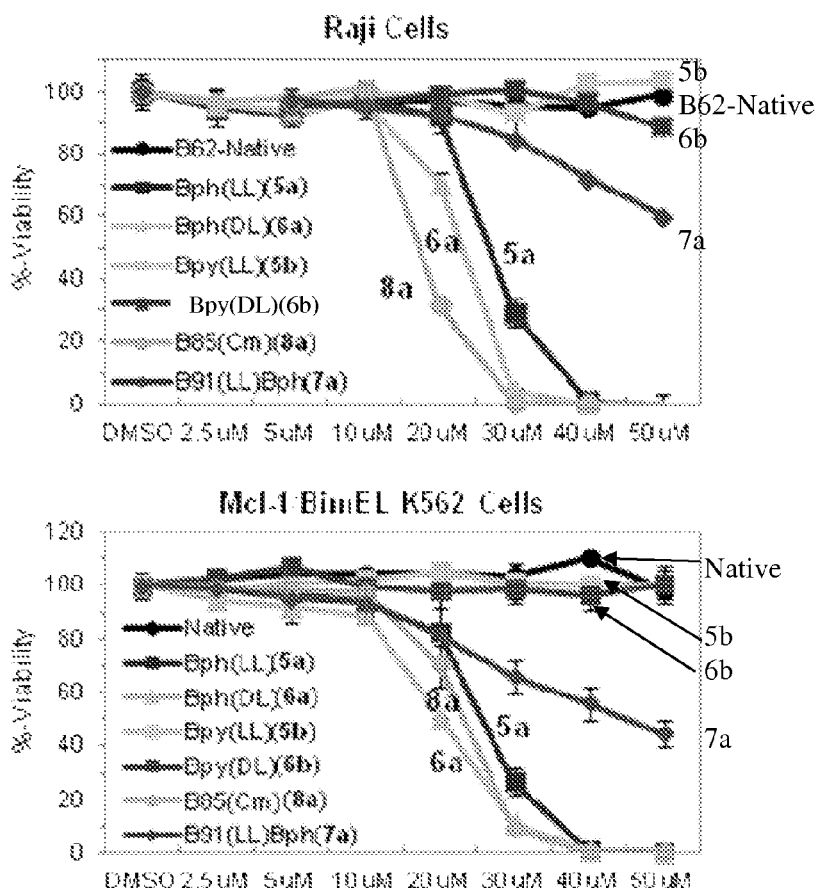
FIG. 14. Cell viability assay after treatment with the linear or the cross-linked NoxaBH3 peptides.

To investigate cellular uptake of the cross-linked peptides, the N-terminal fluorescein-labeled cross-linked NoxaBH3 peptides (5a, 6a, 7a, 8a) and linear peptide Fl-Noxa-(75-93)-C75A were prepared and their uptakes into HeLa cells were examined by both FACS and fluorescence microscopy. Cross-linked peptide 6a and 8a showed robust uptakes after the cells were treated with 10 μM cross-linked peptides for 2 hours (FIG. 13). To examine whether the cross-linked peptides induce apoptosis, Mcl-1-overexpressing Raji cells and K562 cells co-transfected with Mcl-1/BimEL were treated with the cross-linked peptides and the cell viabilities were measured by CellTiter-Glo reagent. The cross-linked peptides 5a, 6a and 8a showed good cellular activity (EC$_{50}$=10-30 μM) (FIG. 14). For Table 5, sequence identifiers for peptides 5a, 5b, 6a, 7a and 8a are the same as shown in Table 3. For the remaining peptides, the following SEQ ID NOs apply: peptide 9a and 10A are SEQ ID NO:17; 11a and 12 a are SEQ ID NO:18; 5c, 5d, 5e, Fluo-5a, Fluo-6a, and Fluo-6b are SEQ ID NO:16; Fluo-NoxaB$^{75-94}$-C75A is SEQ ID NO:15; and Fluo-71 is SEQ ID NO:17.

TABLE 5

ESI-MS Characterization of the Noxa peptides.

| Peptide | Sequence | Mass calculated (M$^+$, m/z) | Mass found (m/z) |
|---|---|---|---|
| NoxaB$^{75-93}$-C75A | AAQLRRIGDKVNLRQKLLN | 2247.7 | 1124.5 [M + 2H]$^{2+}$ |
| 5a | AAC'LRRIGDC'VNLRQKLLN$^a$ | 2377.2 | 1189.4 [M + 2H]$^{2+}$ |
| 5b | AAC"LRRIGDC"VNLRQKLLN$^b$ | 2379.5 | 1190.5 [M + 2H]$^{2+}$ |
| 6a | AAc'LRRIGDC'VNLRQKLLN$^c$ | 2377.7 | 1189.7 [M + 2H]$^{2+}$ |
| 6b | AAc"LRRIGDC"VNLRQKLLN$^d$ | 2379.4 | 1190.2 [M + 2H]$^{2+}$ |
| 7a | AAQLRC'IGDKVNC'RQKLLN | 2364.3 | 1182.2 [M + 2H]$^{2+}$ |
| 8a | AAC'$_m$LRRIGDC'$_m$VNLRQKLLN$^e$ | 2314.5 | 1158.2 [M + 2H]$^{2+}$ |
| 9a | AAC'LRRIGDC'VNLRQKLLNSQPKKKRKV | 3458.2 | 1729.7 [M + 2H]$^{2+}$ |
| 10a | AAc'LRRIGDC'VNLRQKLLNSQPKKKRKV | 3458.2 | 1729.7 [M + 2H]$^{2+}$ |
| 11a | AAC'LRAIGDC'VNLAQALLN | 2148.2 | 1074.8 [M + 2H]$^{2+}$ |
| 12a | AAc'LRAIGDC'VNLAQALLN | 2148.2 | 1074.7 [M + 2H]$^{2+}$ |
| 5c | AAC$^3$LRRIGDC$^3$VNLRQKLLN$^f$ | 2401.3 | 1201.3 [M + 2H]$^{2+}$ |
| 5d | AAC$^4$LRRIGDC$^4$VNLRQKLLN$^g$ | 2399.2 | 1200.4 [M + 2H]$^{2+}$ |
| 5e | AAC$^5$LRRIGDC$^5$VNLRQKLLN$^h$ | 2436.4 | 1218.7 [M + 2H]$^{2+}$ |
| Fluo-NoxaB$^{75-93}$-C75A | FITC-Ahx-AAQLRRIGDKVNLRQKLLN$^i$ | 2705.7 | 1353.9 [M + 2H]$^{2+}$ |

TABLE 5-continued

ESI-MS Characterization of the Noxa peptides.

| Peptide | Sequence | Mass calculated (M⁺, m/z) | Mass found (m/z) |
|---------|----------|---------------------------|------------------|
| Fluo-5a | FITC-Ahx-AAC'LRRIGDC'VNLRQKLLN | 2835.2 | 1418.7 [M + 2H]²⁺ |
| Fluo-6a | FITC-Ahx-AAc'LRRIGDC'VNLRQKLLN | 2835.2 | 1418.9 [M + 2H]²⁺ |
| Fluo-6b | FITC-Ahx-AAc"LRRIGDC"VNLRQKLLN | 2837.2 | 1420.2 [M + 2H]²⁺ |
| Fluo-7a | FITC-Ahx-AAQLRC'IGDKVNC'RQKLLN | 2822.4 | 1412.2 [M + 2H]²⁺ |
| Fluo-8a | FITC-Ahx-AAC'ₘLRRIGDC'ₘVNLRQKLLN | 2772.5 | 1387.3 [M + 2H]²⁺ |

$^a$C' denotes Bph-linked cysteine;
$^b$C" denotes Bpy-linked cysteine;
$^c$c' (lower case) denotes Bph-linked D-cysteine;
$^d$c" (lower case) denotes Bpy-linked D-cysteine'
$^e$C'$_m$ denotes Bph-linked α-methyl-L-cysteine;
$^f$C³ denotes Bdp-linked cysteine;
$^g$C⁴ denotes Bphe-linked cysteine;
$^h$C⁵ denotes Bdp-linked cysteine;
$^i$Ahx = 6-aminohexanoic acid.
The structures of Bph, Bdp, Bphe, and Bdb are shown as follows.

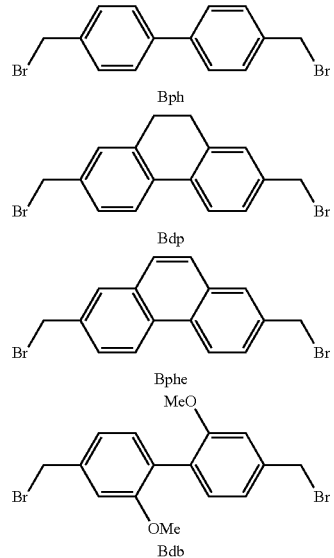

Figure 15:
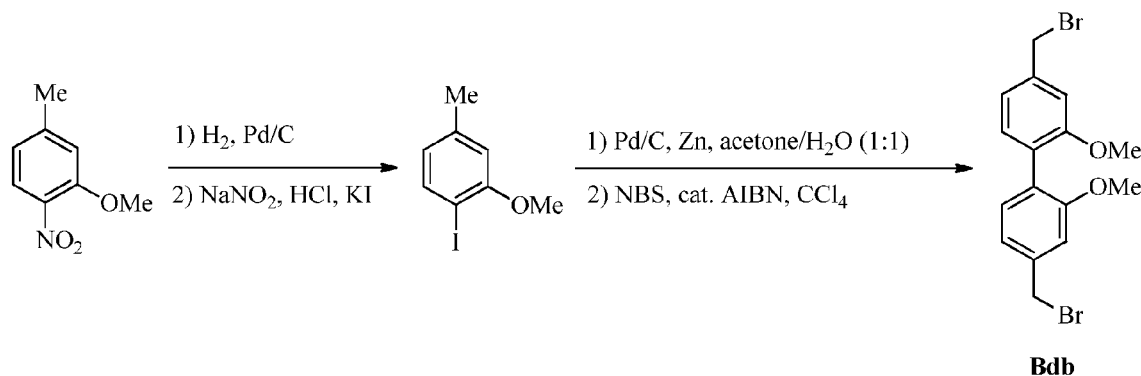
FIG. 15. An example of the synthesis of 4,4'-bis-bromomethyl-2,2'-dimethoxy-biphenyl (Bdb).

Synthesis of 4,4'-bis-bromomethyl-2,2'-dimethoxy-biphenyl (Bdb). Bdb was synthesized according to FIG. 15. Briefly, 1-iodo-5-methylanisole (100 mg, 0.4 mmol) was added in to a mixture of 10% Pd on carbon (100 mg) and zinc powder (100 mg, 1.5 mmol) suspended in 5.2 mL of acetone/water (1:1), and the mixture was stirred at room temperature overnight. The solution was extracted with diethyl ether and the ether layer was collected and dried over anhydrous $Na_2SO_4$. The ether was removed under reduced pressure and the residue was applied to a flash column chromatography to afford 2,2'-dimethoxy-4,4'-dimethyl biphenyl as a yellow solid (42 mg, 46%). The conversion of 2,2'-dimethoxy-4,4'-dimethyl biphenyl to 4,4'-bis-bromomethyl-2,2'-dimethoxy-biphenyl was accomplished by following a previously reported procedure and resulted in a 31% yield.

Competitive Florescence Polarization Assay. The binding affinity of the Noxa peptides toward GST-Mcl-1 was determined in a competitive fluorescence polarization assay with the fluorescein-labeled Bak or Bim. Briefly, fluorescein-labeled Bak was incubated with GST-Mcl-1 in a binding buffer (PBS, 0.005% Tween-20, pH7.4) at room temperature in a 96-well microtiter plate. Various concentrations of Noxa peptides (dissolved in PB-buffer containing 25% DMSO) were added to each well. The final concentrations of fluorescein-labeled Bak and GST-Mcl-1 were 5 nM and 15 nM, respectively. After shaking on Bioshake-iQ at room temperature for 3 minutes, the fluorescence developed in each well was recorded with a PerkinElmer 2030 plate reader with excitation and emission wavelength of 485 nm and 525 nm, respectively. The reading was repeated at various time points to ensure that the competition has reached equilibrium.

Example 3

Figure 16:
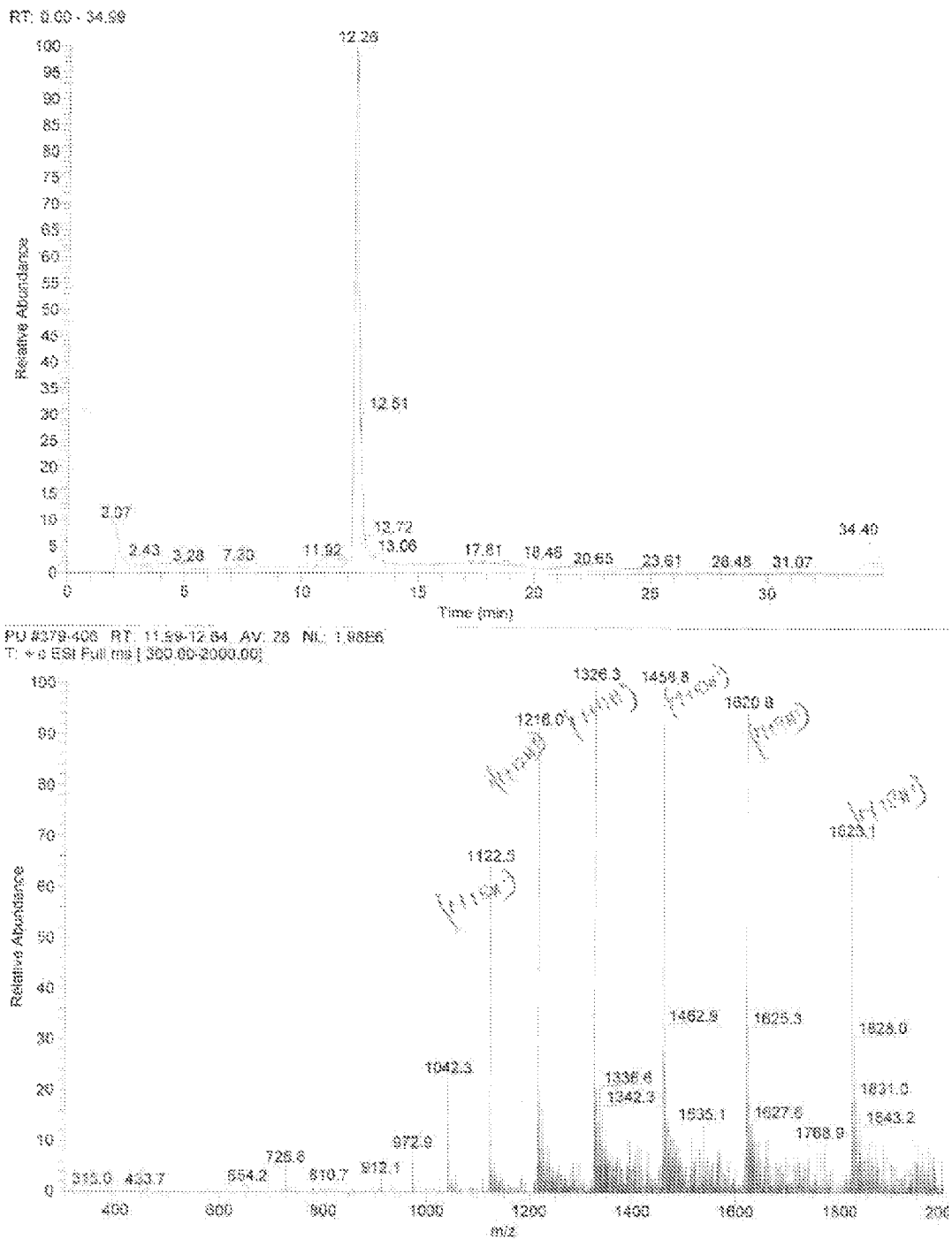
FIG. 16. LC-MS analysis of the Noxa-ubiquitin fusion protein carrying dicysteines at residues 30 and 37 before the Bpy-mediated cross-linking reaction: Top, liquid chromatography traces monitored by ion counts; Bottom, electron-spray derived charge ladders of the intact proteins. The corresponding positive charges were marked for all major peaks.
Figure 17:
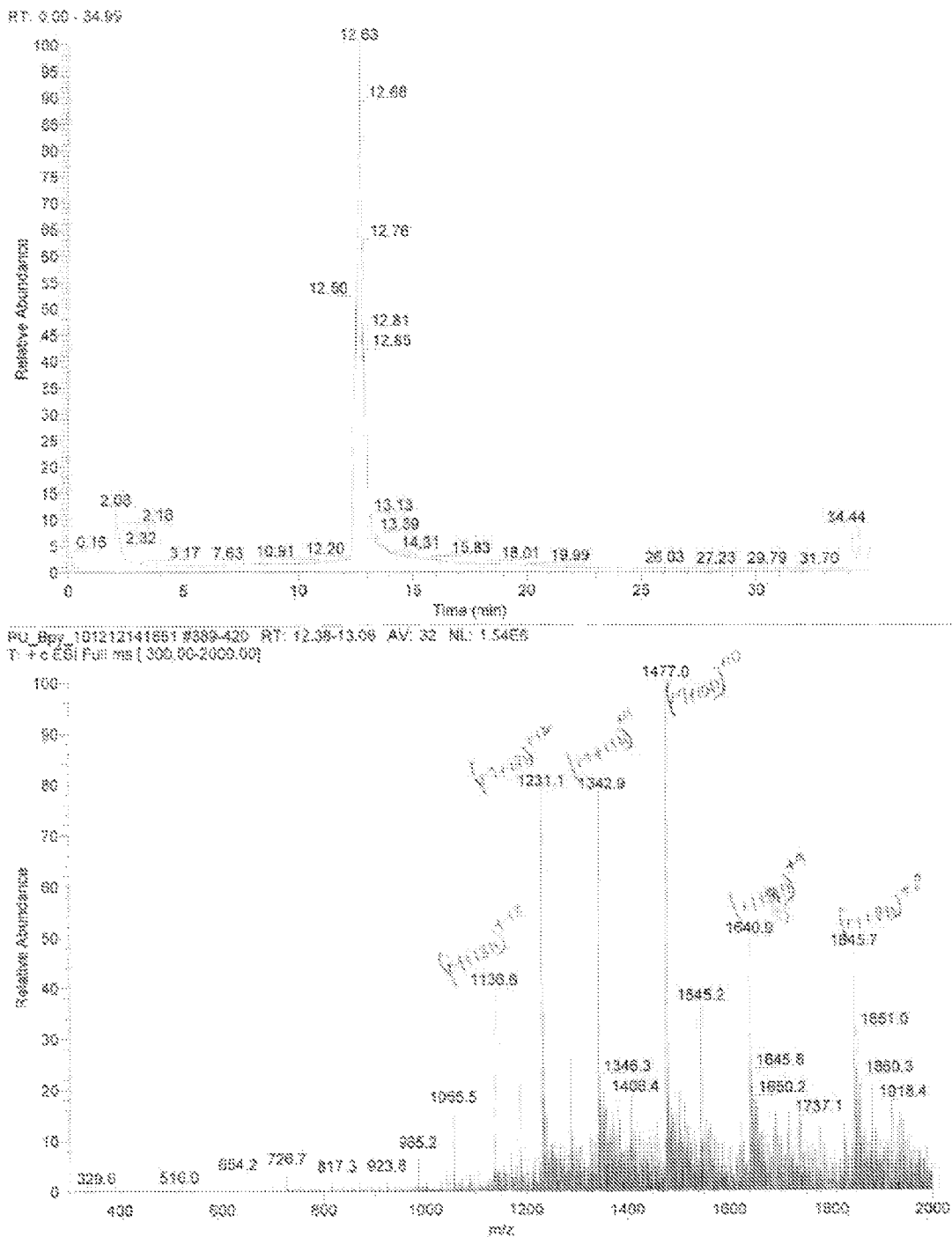
FIG. 17. LC-MS analysis of the Noxa-ubiquitin fusion protein carrying dicysteines at residues 30 and 37 after the Bpy-mediated cross-linking reaction: Top, liquid chromatography traces monitored by ion counts; Bottom, electron-spray derived charge ladders of the intact proteins. The corresponding positive charges were marked for all major peaks.

The cross-linking chemistry also works with proteins containing a helical segment with two cysteines located at the i, i+7 positions. For this purpose, Noxa was fused to the N–1 or C-terminus of ubiquitin to produce Noxa-ubiquitin and ubiquitin-Noxa fusion protein, respectively. After cloning, expression of these two fusion proteins in *E. coli*, and purification with the Ni-NTA affinity column, cross linking using Bpy cross linker was successfully performed with these proteins, generating Noxa-ubiquitin-Bpy and ubiquitin-Noxa-Bpy. The reaction was monitored by LC-MS and the cross-linking efficiency on these proteins was around 85% when calculated using LC-MS data (FIGS. 16 and 17). In the FP assay, the cross-linking proteins showed drastically increased affinity toward Mcl-1 compared to the parent proteins (Table 6).

TABLE 6

Inhibitory activity of Noxa-fused ubiquitin proteins in a competitive FP assay

| Protein Name | IC$_{50}$, Mcl-1 (nM) |
| --- | --- |
| Noxa-ubiquitin | >2,000 |
| Noxa-ubiquitin-Bpy | 7.5 |
| Ubiquitin-Noxa | 160 |
| Ubiquitin-Noxa-Bpy | 5.9 |

Noxa-ubiquitin fusion protein (137 residues)

(SEQ ID NO: 21)
GSSHHHHHHSSGLVPRGSHMPADLKDEAAC̲LRRIGDC̲VNLRQKLLNGGGG

SGGGGSGGGGSMQIFVKTLTGKTITLEVEPSDTIENVKAKIQDKEGIPPD

QQRLIFAGKQLEDGRTLSDYNIQKESTLHLVLRLRGG

Calcd mass: 14581.5. found 14578.5±1.1 (see FIG. 16).
Bpy-cross-linked noxa-ubiquitin fusion protein (SEQ ID NO: 14)
GSSHHHHHHSSGLVPRGSHMPADLKDEAAC̲"LRRIGDC̲"VNLRQKLLNGG

GGSGGGGSGGGGSMQIFVKTLTGKTITLEVEPSDTIENVKAKIQDKEGIP

PDQQRLIFAGKQLEDGRTLSDYNIQKESTLHLVLRLRGG

C̲" denotes Bpy-cross-linked cysteine.
Calcd mass: 14761.6. found 14760.3±1.8 (see FIG. 17).

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A cross-linked protein or peptide having the following structure:

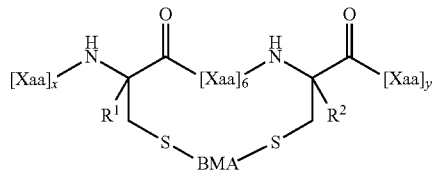

wherein,

[Xaa] is an amino acid and BMA is a bismethylene aryl moiety comprising a $C_{10}$ to $C_{14}$ aryl ring system or a $C_{10}$ to $C_{14}$ heteroaryl ring system, wherein, for a cross-linked peptide x is an integer from 0 to 42, y is an integer from 0 to 42, and x+y is from 0 to 42, or for a cross-linked protein x+y is greater than or equal to 43, wherein, $R^1$ and $R^2$ are each independently a hydrogen or an alkyl group, and wherein, if x is 0, then the terminus of the cross-linked protein or peptide is an amine group and if y is 0, then the terminus of the cross-linked protein or peptide is a carboxylic acid group.

2. The cross-linked protein or peptide of claim 1, wherein the bismethylene aryl (BMA) moiety has the following structure:

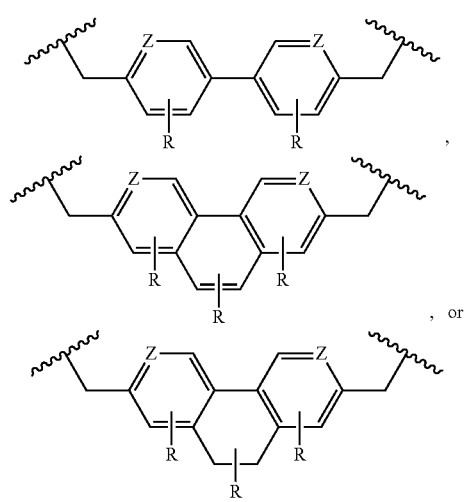

wherein R is, optionally, one or more substituents and is/are hydrogen, halogen, alkyl group, alkoxy group, nitro group, amino group, alkylamino group, trifluoromethyl group or a combination thereof; and Z is nitrogen, carbon, or a combination thereof.

3. The cross-linked protein or peptide of claim 2, wherein the bismethylene aryl (BMA) moiety has the following structure:

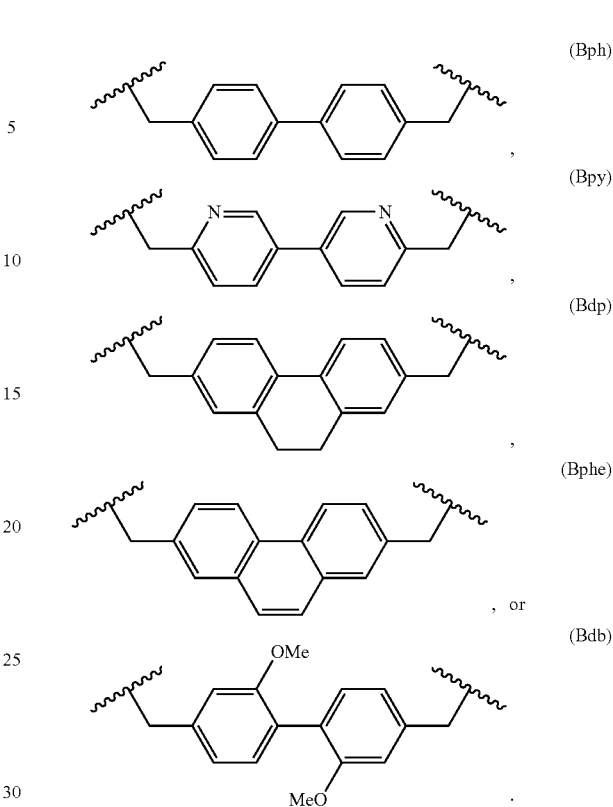

4. The cross-linked protein or peptide of claim 1, wherein the two cysteines connecting the bismethylene aryl moiety are selected from the group consisting of L-cycteine, D-cysteine, α-methyl L-cysteine, α-methyl D-cysteine, and a combination thereof.

5. The cross-linked protein or peptide of claim 1, wherein one or both of the cross-linking cysteine residues is/are D-cysteine.

6. The cross-linked protein or peptide of claim 1, wherein $R^1$ and $R^2$ are hydrogen or methyl.

7. The cross-linked protein or peptide of claim 1, wherein the protein has at least one helical motif.

8. The cross-linked protein or peptide of claim 1, wherein the peptide is conjugated to a fluorophore.

9. The cross-linked protein or peptide of claim 8, wherein the fluorophore is fluorescein or fluorescein isothiocyanate (FITC).

10. The cross-linked protein or peptide of claim 8, wherein the fluorophore molecule is conjugated to the peptide through an aminohexanoic acid moiety.

11. A method for preparation of a cross-linked protein or peptide, comprising the steps of:

a) providing a protein or peptide having the following structure:

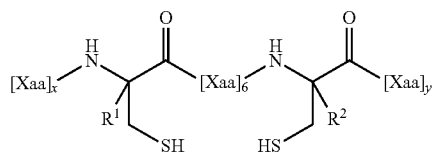

wherein,

[X$_{aa}$] is any amino acid, wherein, for a peptide x is an integer from 0 to 42, y is an integer from 0 to 42, and x+y is from 0 to 42, or for a protein x+y is greater than or equal to 43, and $R_1$ and $R_2$ are each independently a hydrogen or alkyl group; and b) contacting said peptide with a bismethylene aryl linker having the following structure:

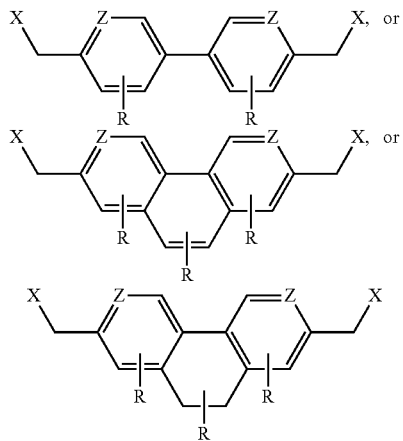

wherein,

X is chloro, bromo, iodo, tosylate, or a combination thereof, and

Z is nitrogen, carbon, or a combination thereof, and

R is, optionally, one or more substituents and is/are hydrogen, halogen, alkyl group, nitro group, amino group, alkylamino group, trifluoromethyl group or a combination thereof;

such that a cross-linked protein or peptide having the following structure:

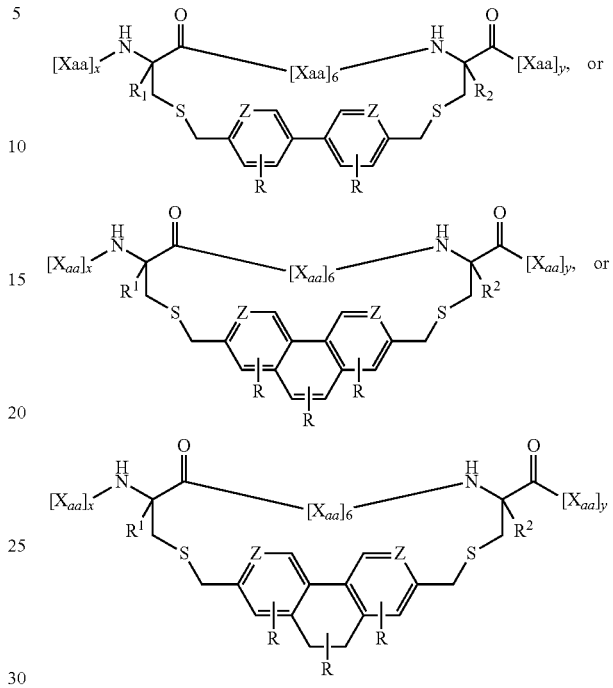

is formed.

12. A composition comprising at least one cross-linked peptide or protein of claim 1 and at least one excipient.

* * * * *

SEQUENCE LISTING

```
<160> NUMBER OF SEQ ID NOS: 21

<210> SEQ ID NO 1
<211> LENGTH: 12
<212> TYPE: PRT
<213> ORGANISM: artificial
<220> FEATURE:
<223> OTHER INFORMATION: fragment of PDI

<400> SEQUENCE: 1

Leu Thr Phe Glu His Tyr Trp Ala Gln Leu Thr Ser
1               5                   10

<210> SEQ ID NO 2
<211> LENGTH: 12
<212> TYPE: PRT
<213> ORGANISM: artificial sequence
<220> FEATURE:
<223> OTHER INFORMATION: sequence for stapled peptide

<400> SEQUENCE: 2

Leu Thr Phe Cys His Tyr Trp Ala Gln Leu Cys Ser
1               5                   10

<210> SEQ ID NO 3
<211> LENGTH: 12
<212> TYPE: PRT
<213> ORGANISM: artificial sequence
<220> FEATURE:
<223> OTHER INFORMATION: sequence for stapled peptide

<400> SEQUENCE: 3

Leu Thr Phe Cys Arg Tyr Trp Ala Arg Leu Cys Ser
1               5                   10

<210> SEQ ID NO 4
<211> LENGTH: 12
<212> TYPE: PRT
<213> ORGANISM: artificial sequence
```

```
<220> FEATURE:
<223> OTHER INFORMATION: sequence for stapled peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 4

Leu Thr Phe Xaa His Tyr Trp Ala Gln Leu Cys Ser
1               5                   10

<210> SEQ ID NO 5
<211> LENGTH: 12
<212> TYPE: PRT
<213> ORGANISM: artificial sequence
<220> FEATURE:
<223> OTHER INFORMATION: sequence for stapled peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 5

Leu Thr Phe Xaa Arg Tyr Trp Ala Arg Leu Cys Ser
1               5                   10

<210> SEQ ID NO 6
<211> LENGTH: 19
<212> TYPE: PRT
<213> ORGANISM: artificial sequence
<220> FEATURE:
<223> OTHER INFORMATION: sequence for stapled peptide

<400> SEQUENCE: 6

Ala Ala Cys Leu Arg Arg Ile Gly Asp Cys Val Asn Leu Arg Gln Lys
1               5                   10                  15

Leu Leu Asn

<210> SEQ ID NO 7
<211> LENGTH: 19
<212> TYPE: PRT
<213> ORGANISM: artificial sequence
<220> FEATURE:
<223> OTHER INFORMATION: sequence for stapled peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 7

Ala Ala Xaa Leu Arg Arg Ile Gly Asp Cys Val Asn Leu Arg Gln Lys
1               5                   10                  15

Leu Leu Asn

<210> SEQ ID NO 8
<211> LENGTH: 19
<212> TYPE: PRT
<213> ORGANISM: artificial sequence
<220> FEATURE:
<223> OTHER INFORMATION: sequence for stapled peptide

<400> SEQUENCE: 8

Ala Ala Gln Leu Arg Cys Ile Gly Asp Lys Val Asn Cys Arg Gln Lys
1               5                   10                  15

Leu Leu Asn
```

```
<210> SEQ ID NO 9
<211> LENGTH: 28
<212> TYPE: PRT
<213> ORGANISM: artificial sequence
<220> FEATURE:
<223> OTHER INFORMATION: sequence for stapled peptide

<400> SEQUENCE: 9

Ala Ala Cys Leu Arg Arg Ile Gly Asp Cys Val Asn Leu Arg Gln Lys
1               5                   10                  15

Leu Leu Asn Ser Gln Pro Lys Lys Lys Arg Lys Val
            20                  25

<210> SEQ ID NO 10
<211> LENGTH: 19
<212> TYPE: PRT
<213> ORGANISM: artificial sequence
<220> FEATURE:
<223> OTHER INFORMATION: sequence for stapled peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 10

Ala Ala Xaa Leu Arg Arg Ile Gly Asp Xaa Val Asn Leu Arg Gln Lys
1               5                   10                  15

Leu Leu Asn

<210> SEQ ID NO 11
<211> LENGTH: 28
<212> TYPE: PRT
<213> ORGANISM: artificial sequence
<220> FEATURE:
<223> OTHER INFORMATION: sequence for stapled peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 11

Ala Ala Xaa Leu Arg Arg Ile Gly Asp Cys Val Asn Leu Arg Gln Lys
1               5                   10                  15

Leu Leu Asn Ser Gln Pro Lys Lys Lys Arg Lys Val
            20                  25

<210> SEQ ID NO 12
<211> LENGTH: 19
<212> TYPE: PRT
<213> ORGANISM: artificial sequence
<220> FEATURE:
<223> OTHER INFORMATION: sequence for stapled peptide

<400> SEQUENCE: 12

Ala Ala Cys Leu Arg Ala Ile Gly Asp Cys Val Asn Leu Ala Gln Ala
1               5                   10                  15

Leu Leu Asn

<210> SEQ ID NO 13
<211> LENGTH: 19
<212> TYPE: PRT
<213> ORGANISM: artificial sequence
<220> FEATURE:
```

```
<223> OTHER INFORMATION: sequence for stapled peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 13

Ala Ala Xaa Leu Arg Ala Ile Gly Asp Cys Val Asn Leu Ala Gln Ala
1               5                   10                  15

Leu Leu Asn

<210> SEQ ID NO 14
<211> LENGTH: 137
<212> TYPE: PRT
<213> ORGANISM: artificial sequence
<220> FEATURE:
<223> OTHER INFORMATION: sequence for stapled peptide
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid

<400> SEQUENCE: 14

Gly Ser Ser His His His His His Ser Ser Gly Leu Val Pro Arg
1               5                   10                  15

Gly Ser His Met Pro Ala Asp Leu Lys Asp Glu Ala Ala Xaa Leu Arg
            20                  25                  30

Arg Ile Gly Asp Xaa Val Asn Leu Arg Gln Lys Leu Leu Asn Gly Gly
        35                  40                  45

Gly Gly Ser Gly Gly Gly Gly Ser Gly Gly Gly Ser Met Gln Ile
    50                  55                  60

Phe Val Lys Thr Leu Thr Gly Lys Thr Ile Thr Leu Glu Val Glu Pro
65                  70                  75                  80

Ser Asp Thr Ile Glu Asn Val Lys Ala Lys Ile Gln Asp Lys Glu Gly
                85                  90                  95

Ile Pro Pro Asp Gln Gln Arg Leu Ile Phe Ala Gly Lys Gln Leu Glu
            100                 105                 110

Asp Gly Arg Thr Leu Ser Asp Tyr Asn Ile Gln Lys Glu Ser Thr Leu
        115                 120                 125

His Leu Val Leu Arg Leu Arg Gly Gly
    130                 135

<210> SEQ ID NO 15
<211> LENGTH: 19
<212> TYPE: PRT
<213> ORGANISM: artificial sequence
<220> FEATURE:
<223> OTHER INFORMATION: sequence for stapled peptide

<400> SEQUENCE: 15

Ala Ala Gln Leu Arg Arg Ile Gly Asp Lys Val Asn Leu Arg Gln Lys
1               5                   10                  15

Leu Leu Asn

<210> SEQ ID NO 16
<211> LENGTH: 19
<212> TYPE: PRT
<213> ORGANISM: artificial sequence
<220> FEATURE:
```

```
<223> OTHER INFORMATION: sequence for stapled peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 16

Ala Ala Xaa Leu Arg Arg Ile Gly Asp Xaa Val Asn Leu Arg Gln Lys
1               5                   10                  15

Leu Leu Asn

<210> SEQ ID NO 17
<211> LENGTH: 19
<212> TYPE: PRT
<213> ORGANISM: artificial sequence
<220> FEATURE:
<223> OTHER INFORMATION: sequence for stapled peptide
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 17

Ala Ala Gln Leu Arg Xaa Ile Gly Asp Lys Val Asn Xaa Arg Gln Lys
1               5                   10                  15

Leu Leu Asn

<210> SEQ ID NO 18
<211> LENGTH: 19
<212> TYPE: PRT
<213> ORGANISM: artificial sequence
<220> FEATURE:
<223> OTHER INFORMATION: sequence for stapled peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 18

Ala Ala Xaa Leu Arg Ala Ile Gly Asp Xaa Val Asn Leu Ala Gln Ala
1               5                   10                  15

Leu Leu Asn

<210> SEQ ID NO 19
<211> LENGTH: 12
<212> TYPE: PRT
<213> ORGANISM: artificial sequence
<220> FEATURE:
<223> OTHER INFORMATION: sequence for stapled peptide
<220> FEATURE:
<221> NAME/KEY: misc_feature
<222> LOCATION: (4)..(4)
<223> OTHER INFORMATION: Xaa can be any naturally occurring amino acid
```

```
<220> FEATURE:
<221> NAME/KEY: misc_feature
<222> LOCATION: (11)..(11)
<223> OTHER INFORMATION: Xaa can be any naturally occurring amino acid

<400> SEQUENCE: 19

Leu Thr Phe Xaa His Tyr Trp Ala Gln Leu Xaa Ser
1               5                  10

<210> SEQ ID NO 20
<211> LENGTH: 12
<212> TYPE: PRT
<213> ORGANISM: artificial sequence
<220> FEATURE:
<223> OTHER INFORMATION: sequence for stapled peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 20

Leu Thr Phe Xaa Arg Tyr Trp Ala Arg Leu Xaa Ser
1               5                  10

<210> SEQ ID NO 21
<211> LENGTH: 137
<212> TYPE: PRT
<213> ORGANISM: artificial sequence
<220> FEATURE:
<223> OTHER INFORMATION: Noxa-ubiquitin fusion

<400> SEQUENCE: 21

Gly Ser Ser His His His His His His Ser Ser Gly Leu Val Pro Arg
1               5                  10                  15

Gly Ser His Met Pro Ala Asp Leu Lys Asp Glu Ala Ala Cys Leu Arg
            20                  25                  30

Arg Ile Gly Asp Cys Val Asn Leu Arg Gln Lys Leu Leu Asn Gly Gly
        35                  40                  45

Gly Gly Ser Gly Gly Gly Gly Ser Gly Gly Gly Gly Ser Met Gln Ile
    50                  55                  60

Phe Val Lys Thr Leu Thr Gly Lys Thr Ile Thr Leu Glu Val Glu Pro
65                  70                  75                  80

Ser Asp Thr Ile Glu Asn Val Lys Ala Lys Ile Gln Asp Lys Glu Gly
                85                  90                  95

Ile Pro Pro Asp Gln Gln Arg Leu Ile Phe Ala Gly Lys Gln Leu Glu
            100                 105                 110

Asp Gly Arg Thr Leu Ser Asp Tyr Asn Ile Gln Lys Glu Ser Thr Leu
        115                 120                 125

His Leu Val Leu Arg Leu Arg Gly Gly
    130                 135
```